United States Patent
Schaefer et al.

(10) Patent No.: US 12,163,130 B2
(45) Date of Patent: *Dec. 10, 2024

(54) COMPOSITIONS AND METHODS FOR MODULATING NEURONAL EXCITABILITY AND MOTOR BEHAVIOR

(71) Applicants: Icahn School of Medicine at Mount Sinai, New York, NY (US); The Rockefeller University, New York, NY (US)

(72) Inventors: Anne Schaefer, New York, NY (US); Paul Greengard, New York, NY (US); Chan Lek Tan, San Francisco, CA (US)

(73) Assignees: Icahn School of Medicine at Mount Sinai, New York, NY (US); The Rockefeller University, New York, NY (US)

( * ) Notice: Subject to any disclaimer, the term of this patent is extended or adjusted under 35 U.S.C. 154(b) by 507 days.

This patent is subject to a terminal disclaimer.

(21) Appl. No.: 17/099,209

(22) Filed: Nov. 16, 2020

(65) Prior Publication Data

US 2021/0317451 A1 Oct. 14, 2021

Related U.S. Application Data

(63) Continuation of application No. 16/148,015, filed on Oct. 1, 2018, now Pat. No. 10,870,853, which is a continuation of application No. 15/032,255, filed as application No. PCT/US2014/062664 on Oct. 28, 2014, now Pat. No. 10,087,443.

(60) Provisional application No. 61/898,952, filed on Nov. 1, 2013, provisional application No. 61/896,463, filed on Oct. 28, 2013.

(51) Int. Cl.
| | |
|---|---|
| *C12N 15/113* | (2010.01) |
| *A01K 67/0275* | (2024.01) |
| *A01K 67/0276* | (2024.01) |
| *A61K 38/18* | (2006.01) |
| *A61K 49/00* | (2006.01) |
| *A61P 25/00* | (2006.01) |
| *A61P 25/08* | (2006.01) |
| *G01N 33/50* | (2006.01) |

(52) U.S. Cl.
CPC ........ *C12N 15/113* (2013.01); *A01K 67/0275* (2013.01); *A01K 67/0276* (2013.01); *A61K 38/185* (2013.01); *A61K 49/0008* (2013.01); *G01N 33/5058* (2013.01); *A01K 2217/052* (2013.01); *A01K 2217/075* (2013.01); *A01K 2217/203* (2013.01); *A01K 2227/105* (2013.01); *A01K 2267/0356* (2013.01); *A61P 25/00* (2018.01); *A61P 25/08* (2018.01); *C12N 2310/141* (2013.01); *C12N 2310/315* (2013.01); *C12N 2310/321* (2013.01); *C12N 2310/341* (2013.01); *C12N 2310/346* (2013.01); *C12N 2310/3515* (2013.01); *C12N 2310/3521* (2013.01)

(58) Field of Classification Search
CPC . C12N 15/113; C12N 2310/141; A61P 25/00; A61P 25/08
See application file for complete search history.

(56) References Cited

U.S. PATENT DOCUMENTS

| | | | |
|---|---|---|---|
| 9,434,945 | B2 | 9/2016 | Faden |
| 2002/0028783 | A1 | 3/2002 | O'Brien |
| 2012/0115919 | A1 | 5/2012 | Mueller |
| 2014/0051746 | A1 | 2/2014 | Naar |
| 2014/0235696 | A1 | 8/2014 | Henshall |
| 2016/0369270 | A1 | 12/2016 | Henshall |
| 2017/0065662 | A1 | 3/2017 | Blain |
| 2019/0144858 | A1 | 5/2019 | Schaefer et al. |

FOREIGN PATENT DOCUMENTS

| | | |
|---|---|---|
| CN | 103656685 | 3/2014 |
| EP | 2623095 | 8/2013 |
| JP | 2013091611 | 5/2013 |
| WO | 9703689 | 2/1997 |
| WO | 1998010785 | 3/1998 |
| WO | 2006070292 | 7/2006 |
| WO | 2006137941 | 12/2006 |
| WO | 2010008588 | 1/2010 |
| WO | 2012023132 | 2/2012 |
| WO | 2013045652 | 4/2013 |
| WO | 2013150303 A1 | 10/2013 |
| WO | 2014096418 | 6/2014 |

OTHER PUBLICATIONS

Menon and Shorvon, Epilepsy Research, 87:1-11 (Year: 2009).*
Xu et al., "The effects of brain-derived neurotrophic factor (bdnf) administration on kindling induction, Trk expression and seizure-related morphological changes," Neuroscience, vol. 126, pp. 521-531, 2004.

(Continued)

*Primary Examiner* — Kimberly Ballard
*Assistant Examiner* — Stacey N MacFarlane
(74) *Attorney, Agent, or Firm* — Heslin Rothenberg Farley & Mesiti P.C.

(57) ABSTRACT

The invention is directed to compositions and methods for treating or reducing the likelihood of the development of epilepsy in an individual. The method comprises administering to the central nervous system of an individual in need of such treatment a therapeutically effective amount of an agent capable of increasing the expression and/or activity of miR-128.

20 Claims, 33 Drawing Sheets

Specification includes a Sequence Listing.

(56) References Cited

OTHER PUBLICATIONS

Godlewski et al., "Targeting of the Bmi-1 Oncogene/Stem Cell Renewal Factor by MicroRNA-128 Inhibits Glioma Proliferation and Self-Renewal," Cancer Research, vol. 68, No. 22, pp. 9125-9130, Nov. 15, 2008.
Paradiso et al., "Localized delivery of fibroblast growth factor-2 and brain-derived neurotrophic factor reduces spontaneous seizures in an epilepsy model," PNAS, vol. 106, No. 17, pp. 7191-7196, Apr. 28, 2009.
Evangelisti et al., "MiR-128 up-regulation inhibits Reelin and DCX expression and reduces neuroblastoma cell motility and invasiveness," The FASEB Journal, vol. 23, No. 12, pp. 4276-4287, XP055376014, Aug. 27, 2009.
Kawashima et al., "Glucocorticoid attenuates brain-derived neurotrophic factor-dependent upregulation of glutamate receptors via the suppression of microRNA-132 expression," Neuroscience, New York, NY, US, vol. 165, No. 4, pp. 1301-1311, XP027027970, Feb. 17, 2010.
Lee et al., "Altered microRNA regulation in Huntington's disease models," Experimental Neurology, Elsevier, Amsterdam, NL, vol. 227, No. 1, pp. 172-179, XP027585906, Oct. 28, 2010.
Ceulemans "Overall management of patients with Dravet Syndrome : Review," Developmental Medicine and Child Neurology, vol. 53, pp. 19-23, XP055376281, Apr. 19, 2011.
Pichardo-Casas et al., "Expression profiling of synaptic microRNAs from the adult rat brain identifies regional differences and seizure-induced dynamic modulation," Brain Research, Elsevier, Amsterdam, NL, vol. 1436, pp. 20-33, XP028445123, Dec. 9, 2011.
Tsai et al., "Brain-Derived Neurotrophic Factor Ameliorates Brain Stem Cardiovascular Dysregulation during Experimental Temporal Lobe Status Epilepticus," PLOS ONE, vol. 7, Issue 3, e33527, Mar. 2012.
Shi et al., "MiR-128 Inhibits Tumor Growth and Angiogenesis by Targeting p70S6K1," PLOS ONE, vol. 7, No. 3, p. e32709, XP055376081, Mar. 19, 2012.
O'Carroll et al., "General Principals of miRNA Biogenesis and Regulation in the Brain," Neuropsychopharmacology, vol. 38, No. 1, pp. 39-54, XP055391620, Jun. 6, 2012.
Jimenez-Mateos et al. "Silencing microRNA-134 produces neuroprotective and prolonged seizure-suppressive effects" Nature Medicine 18(7): 1087-1094; Jul. 2012.
Jimenez-Mateos et al., "Epilepsy and microRNA," Neuroscience, vol. 238, pp. 218-229, XP055376061, Feb. 26, 2013.
Tan, "Tuning of Neuronal Excitation by a Brain Specific Microrna MIR-128: From Targets to Behavior. Ph.D. Thesis," Student Theses and Dissertations, pp. i-vii, 1-154, XP055370606, Jun. 2013.
Dogini et al., "MicroRNA regulation and dysregulation in epilepsy," Frontiers in Cellular Neuroscience, vol. 7, XP055376059, Oct. 4, 2013.
Bot et al., "Alterations in miRNA Levels in the Dentate Gyrus in Epileptic Rats," PLOS ONE, vol. 8, No. 10, p. e76051, XP055172903, Oct. 11, 2013.
Tan et al., "MicroRNA-128 Governs Neuronal Excitability and Motor Behavior in Mice," Science, vol. 342, No. 6163, pp. 1254-1258, XP055370611, Dec. 6, 2013.
Kretschmann et al., "Different MicroRNA Profiles in Chronic Epilepsy Versus Acute Seizure Mouse Models", J Mol Neurosci. Feb. 2015; 55: 466-479.
Yuan et al., "Dysregulation of microRNA-128 expression in WHO grades 2 glioma is associated with glioma-associated epilepsy Down-regulation of miR-128 induces glioma-associated seizure," Epilepsy Research, vol. 127, pp. 6-11, 2016.
Supplementary European Search Report for EP 14857152.4, Oct. 30, 2017, 15 pages.
Kandratavicius et al.m "Animal models of epilepsy: use and limitations ", Neuropsychiatric Disease and Treatment, vol. 2014, No. 10, pp. 1693-1705, 2014.
Adamolekun, B., "Seizure Disorders," MSD Manual Professional Version (English Machine Translation) (2013).
Adlakha and Saini, "Brain MicroRNAs and Insights Into Biological Functions and Therapeutic Potential of Brain Enriched miRNA-128," Molecular Cancer 13:33, pp. 1-18 (2014).
Adlakha et al., "Pro-Apoptotic MiRNA-128-2 Modulates ABCA1, ABCG1 and RXRα Expression and Cholesterol Homeostasis," Cell Death and Disease 4:e780 (2013).
Cheah et al., "Specific Deletion of Nav1.1 Sodium Channels in Inhibitory Interneurons Causes Seizures and Premature Death in a Mouse Model of Dravet Syndrome," PNAS 109(36):14646-51 (2012).
Chiron and Dulac, "The Pharmacologic Treatment of Dravet Syndrome," Epilepsia 52(Suppl. 2):72-75 (2011).
Jin et al., "miRNA-128 Suppresses Prostate Cancer by Inhibiting BMI-1 to Inhibit Tumor-Initiating Cells," Cancer Research 74:15, 13 pages (2014).
Kearney, J.A., "Cognitive and Social Impairment in Mouse Models Mirrors Dravet Syndrome," Epilepsy Currents 13(2):97-99 (2013).
Liu and Xu, "MicroRNA in Central Nervous System Trauma and Degenerative Disorders," Physiol. Genomics 43:571-80 (2011).
Nakajima, M., "MicroRNAs Regulating Metabolism of Drugs, Xenobiotics and Endobiotics," The Showa University Journal of Pharmaceutical Sciences 4(1):1-11 (2013) (English abstract).
Wirrell, E.C., "Treatment of Dravet Syndrome," The Canadian Journal of Neurological Sciences 43:S13-S18 (2016).
Lewis, B.P., et al., "Prediction of Mammalian MicroRNA Targets", Cell, vol. 115, pp. 787-798 (2003).
Lewis, B.P., et al., "Conserved Seed Pairing, Often Flanked by Adenosines, Indicates that Thousands of Human Genes are MicroRNA Targets", Cell, vol. 120, pp. 15-20 (2005).
Guidi, M., et al., "Overexpression of miR-128 specifically inhibits the truncated isoform of NTRK3 and upregulates BCL2 in SH-SY5Y neuroblastoma cells", BMC Molecular Biology, vol. 11, No. 95, pp. 1-17 (2010).
International Search Report and Written Opinion of the International Searching Authority for International Application No. PCT/US2014/062664 mailed on Feb. 25 2015.
Yasuhiro et al. (2016), Gene Silencing by miRNA-like siRNA, Reports of Faculty of Humanity-Oriented Science and Engineering, Kindai University, issue 25, pp. 1-6.
Official Action mailed by the Japanese Patent Office in connection with Japanese Patent Application No. 2020-079949 on Jun. 1, 2021 (English translation).
Molin Li et al., "miR-128 and its target genes in tumorigenesis and metastasis," Experimental Cell Research, vol. 319, p. 3059-3064 (2013).
Shetty, "Neural Stem Cell Therapy for Temporal Lobe Epilepsy," Jasper's Basic Mechanisms of the Epilepsies, 2012.
Goldberg et al., "Mechanisms of epileptogenesi: a convergence on neural circuit dysfunction," Nature Reviews. Neuroscience, 2013, 14(5):337-347.
Hirsch et al., "Abbreviated report of the NIH/NINOS workshop on sudden unexpected death in epilepsy." Neurology 76: 1932-1938. (Year: 2011).
Jeong et al., "Human Neural Stem Cell Transplantation Promotes Functional Recovery in Rats With Experimental Intracerebral Hemorrhage." Stroke 34: 2258-2263. (Year: 2003).
Jing et al., "The combined therapy of intrahippocampal transplantation of adult neural stem cells and intraventricular erythropoietin-infusion ameliorates spontaneous recurrent seizures by suppression of abnormal mossy fiber sprouting." Brain Res 1295: 203-217. (Year: 2009).

* cited by examiner

A

B

Table 1

| ID | Accession | RPM | Chromosome | Start | End | Strand | Confidence | Fetch |
|---|---|---|---|---|---|---|---|---|
| aca-mir-128-1 | MI0018728 | - | 6 | 42720735 | 42720830 | + | - | ☐ |
| aca-mir-128-2 | MI0018729 | - | 1 | 96668145 | 96668238 | + | - | ☐ |
| age-mir-128 | MI0002522 | - | | | | | - | ☐ |
| bta-mir-128-1 | MI0004755 | 1.94e+03 | chr2 | 62007752 | 62007833 | - | - | ☐ |
| bta-mir-128-2 | MI0009727 | 761 | chr22 | 9738598 | 9738681 | + | - | ☐ |
| ccr-mir-128 | MI0023315 | - | | | | | - | ☐ |
| cfa-mir-128-1 | MI0008032 | - | chr19 | 38435956 | 38436011 | + | - | ☐ |
| cfa-mir-128-2 | MI0008057 | - | chr23 | 5826463 | 5826520 | + | - | ☐ |
| cgr-mir-128 | MI0020391 | - | | | | | - | ☐ |
| dre-mir-128-1 | MI0001980 | 41.7 | 22 | 12504146 | 12504243 | + | ✓ | ☐ |
| dre-mir-128-2 | MI0001981 | 265 | 19 | 44518214 | 44518336 | + | - | ☐ |
| eca-mir-128-1 | MI0012821 | - | chr16 | 49087163 | 49087246 | - | - | ☐ |
| eca-mir-128-2 | MI0012838 | - | chr18 | 19492350 | 19492419 | + | - | ☐ |
| fru-mir-128-1 | MI0003421 | - | HE602542.1 | 3829436 | 3829520 | + | - | ☐ |
| fru-mir-128-2 | MI0003346 | - | HE602546.1 | 1445834 | 1445905 | - | - | ☐ |

Figure 18A

| ID | Accession | RPM | Chromosome | Start | End | Strand | Confidence | Fetch |
|---|---|---|---|---|---|---|---|---|
| gga-mir-128-1 | MI0001217 | - | chr7 | 30116396 | 30116477 | + | - | ☐ |
| gga-mir-128-2 | MI0001192 | - | chr2 | 46095828 | 46095909 | + | - | ☐ |
| ggo-mir-128 | MI0020629 | - | 2b | 22767261 | 22767369 | + | - | ☐ |
| hsa-mir-128-1 | MI0000447 | 1.66e+03 | chr2 | 136422967 | 136423048 | + | ✓ | ☐ |
| hsa-mir-128-2 | MI0000727 | 1.53e+03 | chr3 | 35785968 | 35786051 | + | - | ☐ |
| ipu-mir-128-1 | MI0024484 | - | | | | | - | ☐ |
| ipu-mir-128-2 | MI0024483 | - | | | | | - | ☐ |
| mdo-mir-128a | MI0005293 | - | chr6 | 290241098 | 290241181 | - | - | ☐ |
| mdo-mir-128b | MI0023827 | - | chr4 | 132653246 | 132653301 | + | - | ☐ |
| mml-mir-128a | MI0002518 | - | 13 | 116513188 | 116513269 | - | - | ☐ |
| mml-mir-128b | MI0007617 | - | 2 | 178154004 | 178154087 | + | - | ☐ |
| mmu-mir-128-1 | MI0000155 | 2.39e+03 | chr1 | 128202361 | 128202430 | + | ✓ | ☐ |
| mmu-mir-128-2 | MI0000726 | 2.39e+03 | chr9 | 112118636 | 112118711 | - | ✓ | ☐ |
| oan-mir-128-1 | MI0006787 | - | Contig29001 | 34 | 104 | - | - | ☐ |
| oan-mir-128-2 | MI0006892 | - | Ultra389 | 820000 | 820110 | - | - | ☐ |
| ola-mir-128 | MI0019482 | - | 11 | 21614207 | 21614306 | - | - | ☐ |
| pma-mir-128-1 | MI0017060 | - | GL476334.1 | 422133 | 422221 | + | - | ☐ |
| pma-mir-128-2 | MI0017061 | - | GL477033.1 | 40713 | 40801 | + | - | ☐ |

Figure 18B

| ID | Accession | RPM | Chromosome | Start | End | Strand | Confidence | Fetch |
|---|---|---|---|---|---|---|---|---|
| ppa-mir-128 | MI0002523 | - | | | | | - | ☐ |
| ppy-mir-128-1 | MI0002520 | - | 2b | 24605741 | 24605822 | + | - | ☐ |
| ppy-mir-128-2 | MI0014819 | - | 3 | 111073058 | 111073141 | - | - | ☐ |
| ptr-mir-128-1 | MI0002519 | - | 2B | 139615981 | 139616062 | + | - | ☐ |
| ptr-mir-128-2 | MI0008482 | - | 3 | 36312083 | 36312165 | + | - | ☐ |
| mo-mir-128-1 | MI0000900 | - | 13 | 40907575 | 40907656 | + | - | ☐ |
| mo-mir-128-2 | MI0000901 | - | 8 | 116727237 | 116727320 | - | - | ☐ |
| sha-mir-128 | MI0019625 | - | GL849609.1 | 2503876 | 2504025 | + | - | ☐ |
| sla-mir-128 | MI0002521 | - | | | | | - | ☐ |
| ssc-mir-128-1 | MI0002451 | - | chr15 | 18661614 | 18661695 | - | - | ☐ |
| ssc-mir-128-2 | MI0013094 | - | chr13 | 22859191 | 22859270 | + | - | ☐ |
| tgu-mir-128-1 | MI0013712 | - | chr7 | 33186771 | 33186841 | + | - | ☐ |
| tgu-mir-128-2 | MI0013711 | - | chr2 | 28894377 | 28894466 | - | - | ☐ |
| tni-mir-128-1 | MI0003422 | - | 3 | 4160307 | 4160378 | - | - | ☐ |
| tni-mir-128-2 | MI0003347 | - | 21 | 1237202 | 1237273 | - | - | ☐ |
| xtr-mir-128-1 | MI0004932 | - | GL172713.1 | 3010851 | 3010933 | - | - | ☐ |
| xtr-mir-128-2 | MI0004828 | - | GL173401.1 | 415153 | 415232 | + | - | ☐ | see url: www.mirbase.org/cgi-bin/mirna_summary.pl?fam=MIPF0000048

Figure 18C

SEQUENCE LISTING

<160> NUMBER OF SEQ ID NOS: 28

<210> SEQ ID NO 1
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 1
ucacagugaa ccggucucuu u                                          21

<210> SEQ ID NO 2
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 2
ccttcatgtt atgccctcat ccctttatca cacaaatctg tgtagttttc ggcgcgccat    60
tcgccctata gtgagtcg                                              78

<210> SEQ ID NO 3
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 3
aatcttctaa atttccattt gagcacctag ttcatatgta atttagattc ctcgaggctt    60
ggcgtaatca tggtc                                                 75

<210> SEQ ID NO 4
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 4
cgaaaaatat tttcatttat tcttcgaaac tttcatacat tcatacaatg tggcgcgcca    60
ttcgccctat agtgagtcg                                             79

<210> SEQ ID NO 5
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 5
tcaggcctgc cagccttctg tctactgttt aatgactgac agccagtgaa ctcgaggctt    60
ggcgtaatca tggtc                                                 75

<210> SEQ ID NO 6
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 6
aattgcatcg catgggtcac gacgagatcc cgggc     35

<210> SEQ ID NO 7
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 7
aattgcccgg gatctcgtcg tgacccatgc gatgc     35

<210> SEQ ID NO 8
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 8
ctagaataac ttcgtatagc atacattata cgaagttatg aattct     46

<210> SEQ ID NO 9
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 9
ctagagaatt cataacttcg tataatgtat gctatacgaa gttatt     46

<210> SEQ ID NO 10
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 10
ggaagttcct atactttcta gagaatagga acttcggaat aggaacttca gagctcatcg     60
agcccgggta gacggccc     78

<210> SEQ ID NO 11
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 11
gtctacccgg gctcgatgag ctctgaagtt cctattccga agttcctatt ctctagaaag     60
tataggaact tccagct     77

<210> SEQ ID NO 12
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 12 gtaccccgg gataacttcg tatagcatac attatacgaa gttataagct tc     52

<210> SEQ ID NO 13
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 13
gtacgaagct tataacttcg tataatgtat gctatacgaa gttatcccgg gg    52

<210> SEQ ID NO 14
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 14
agctaataac ttcgtatagc atacattata cgaagttatg gatcct    46

<210> SEQ ID NO 15
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 15
agctaggatc cataacttcg tataatgtat gctatacgaa gttatt    46

<210> SEQ ID NO 16
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 16
agctaggatc cataacttcg tataatgtat gctatacgaa gttatt    46

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ccgcaatgct gcctatattc    20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
gcctgaagaa cgagatcagc    20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
gcagtcatgc aagcagctat                                             20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
cgccttttag tttcccacag                                             20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
gaccacacag caagcaggta                                             20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
aaagacggga ccattcacat                                             20

<210> SEQ ID NO 23
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 23
tctctcgtgg gatcattgtt t                                           21

<210> SEQ ID NO 24
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 24
aaaggcgcgc cacgtgacta aaaggcgcga ggagat                           36

<210> SEQ ID NO 25
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 25
aaaggcgcgc ctacgcattc ctgtacggtt g                                31

<210> SEQ ID NO 26

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gagttctctg ctgcctcctg                                              20

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
ggaaagtccc tattggcgtt a                                            21

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
tgctgcataa aaccccagat                                              20
```

COMPOSITIONS AND METHODS FOR MODULATING NEURONAL EXCITABILITY AND MOTOR BEHAVIOR

CROSS-REFERENCE TO RELATED APPLICATIONS

This application is a continuation of U.S. application Ser. No. 16/148,015 filed on Oct. 1, 2018, as a continuation of U.S. application Ser. No. 15/032,255 filed on Apr. 26, 2016, as a national stage filing under 35 U.S.C. § 371 of PCT/US2014/062664 filed Oct. 28, 2014, which claims the benefit of U.S. provisional patent application Ser. No. 61/896,463, filed Oct. 28, 2013, and Ser. No. 61/898,952, filed Nov. 1, 2013; the entire disclosures of which are incorporated herein by reference.

FEDERALLY-FUNDED RESEARCH

This invention was made with government support under DA025962 awarded by the National Institutes of Health and W81XWH-09-1-0095 awarded by the Department of the Army-USAMRAA. The government has certain rights in this invention.

This application contains a sequence listing, created on Feb. 26, 2018; the file, in ASCII format, is designated H1888928.txt and is 6.4 kilobytes in size. The sequence listing file is hereby incorporated by reference in its entirety into the application.

TECHNICAL FIELD

The invention relates to the field of molecular biology. More particularly, it concerns methods and compositions involving microRNA (miRNAs) molecules. In particular, the disclosure also relates to a therapeutic strategy to treat or prevent the development of seizure-related disorders and neurologic injuries.

BACKGROUND OF THE INVENTION

A seizure is a paroxysmal event due to abnormal, excessive, hypersynchronous discharges from an aggregate of central nervous system (CNS) neurons, while epilepsy is a condition in which a person has recurrent seizures due to a chronic, underlying process. Experimental and clinical data indicate that the occurrence of repeated seizures can lead to an epileptic condition. It is therefore of great interest to identify possible pharmacological treatments for seizures, and the time-frame in which such treatment is effective.

Epilepsy is a brain disorder characterized by periodic and unpredictable seizures caused by the rhythmic firing of large groups of neurons. The behavioral manifestations of epileptic seizures in human patients range from mild twitching of an extremity to loss of consciousness and uncontrollable convulsions. Up to 1% of the population is afflicted, making epilepsy one of the most common neurological problems. The abnormal activity associated with epilepsy generates plastic changes in cortical circuitry that play a part in the pathogenesis of the disease. Over a period of time, a weak stimulus that initially had no effect will eventually cause full-blown seizures. This phenomenon is essentially permanent; even after an interval of a year; the same weak stimulus will again trigger a seizure.

Research has focused on where seizures originate and the mechanisms that make the affected region hyperexcitable. Evidence suggests that abnormal activity in cerebral cortex foci provide the triggers for a seizure that then spreads to other synaptically connected regions. Epileptic seizures can be caused by a variety of acute or congenital factors, including cortical damage from trauma, stroke, tumors, congenital cortical dysgenesis, and congenital vascular malformations.

No effective prevention or cure exists for epilepsy. Pharmacological therapies that successfully inhibit seizures are based on two general strategies. One approach is to enhance the function of inhibitory GABAergic synapses; the other is to limit action potential firing by acting on voltage-gated Na+ channels. Commonly used antiseizure medications include carbamazepine, phenobarbital, phenyloin, and valproic acid. These agents must be taken daily, and only inhibit seizures in 60-70% of patients. Thus, there is a large group of patients suffering from epilepsy for whom there is currently no effective treatment.

MicroRNAs (miRNAs or miRs) are a small non-coding family of 19-25 nucleotide RNAs that regulate gene expression by targeting messenger RNAs (mRNA) in a sequence specific manner, inducing translational repression or mRNA degradation depending on the degree of complementarity between miRNAs and their targets (Bartel, D. P. (2004) Cell 116, 281-297). Many miRNAs are conserved in sequence between distantly related organisms, suggesting that these molecules participate in essential processes. Indeed, miRNAs are involved in the regulation of gene expression during development, cell proliferation, apoptosis, glucose metabolism, stress resistance and cancer. There have been considerable efforts made to understand and characterize the temporal, spatial and cellular expression levels and patterns of expression of miRNAs to ascertain their precise role in cellular development and differentiation in both normal and disease states.

Although miRNAs have been shown to be involved in regulation of gene expression under different conditions, e.g. cancer or apoptosis, there is little if any art focusing on miRNA involvement in epilepsy and/or seizures. Thus, there remains a need to provide other alternatives and effective treatments for epilepsy and related disorders, especially those where existing treatments do not provide any remedy for patients.

SUMMARY OF THE INVENTION

The present disclosure relates to a therapeutic strategy to treat or reduce the likelihood of the development of seizure-related disorders and neurologic injuries. The inventors of the instant application have surprisingly discovered a role for miR-128 in neuronal signaling, and in particular a role for miR-128 in modulation of signaling pathways that control neuronal excitability and motor activity.

In one aspect, the present disclosure is directed to a method for treating or reducing the likelihood of the development of epilepsy or status epilepticus in an individual at risk for or suspected of having a condition characterized by seizures, comprising administering to an individual in need of such treatment a therapeutically effective amount of an agent capable of increasing the expression and/or activity of miR-128. In one embodiment, the individual displays symptoms of or has been diagnosed with Dravet Syndrome. In one embodiment, the agent is administered intrathecally or intranasally. In another embodiment, the agent is administered to the central nervous system of the individual. In a particular embodiment, the administration is directly to the hippocampus and/or cortex.

In one embodiment, the agent is miR-128, or is an agent with 90 percent or more sequence homology to miR-128. In a particular embodiment, the agent capable of increasing and/or activating miR-128 is selected from the group consisting of chemically stabilized miR-128, an miR-129 mimic, a nucleic acid encoding miR-128, and a viral vector encoding miR-128. In one embodiment, the agent capable of increasing and/or activating miR-128 is brain-derived neurotrophic factor.

One aspect of the present disclosure is directed to a method for treating or reducing the likelihood of the development or occurrence of seizures in an individual, comprising administering to an individual in need of such treatment a therapeutically effective amount of an agent capable of increasing the expression and/or activity of miR-128, wherein said patient has a brain-related disorder characterized by development of seizures. In one embodiment, the individual is diagnosed with Dravet Syndrome. The agent may be administered intrathecally or intranasally. In one embodiment, the agent is administered to the hippocampus and/or cortex. In one embodiment, the brain-related disorder characterized by development of seizures is selected from the group consisting of stroke, hypoxia, traumatic brain injury, infection, tumor, neurodegenerative disorders, metabolic and autoimmune disorders causing seizures.

Another aspect of the present disclosure is directed to a method for treating or reducing the likelihood of the development of epilepsy in an individual, comprising administering to the individual in need of such treatment a therapeutically effective amount of an agent capable of increasing the expression and/or activity of miR-128, wherein said individual has suffered a prior brain injury that increases said individual's risk of epilepsy. In one embodiment, the brain injury is caused by stroke.

In one aspect, the present disclosure is a pharmaceutical composition for use in treating or reducing the likelihood of the development of a neuronal pathology characterized by seizures comprising an agent capable of increasing the expression and/or activity of miR-128 in combination with a pharmaceutically acceptable excipient. The agent capable of enhancing miR-128 activity may be selected from the group consisting of chemically stabilized miR-128, a miR-128 mimic or a nucleic acid encoding miR-128; agents capable of enhancing expression of miR-128 include, for example, a viral vector encoding miR-128. In another aspect, the present disclosure is directed to an agent capable of increasing miR-128 expression and/or activity for use in reducing the likelihood of spontaneous recurrent seizures in an individual or as an anti-epileptogenic agent in an individual having a brain injury likely to precipitate epilepsy, wherein the agent is delivered to the brain of the individual. In one embodiment, the therapeutic agent (for example miR-128 or an agent with 90 percent or more sequence homology to miR-128) may be directly administered, for example by injection, to certain brain regions, including the hippocampus and/or cortex.

One aspect of the present disclosure is directed to a method of identifying compounds useful in the treatment or reducing the likelihood of a pathology characterized by seizures, comprising contacting a miR-128-expressing cell with a candidate compound, and determining the level of activity of the miR-128-expressing cell, wherein an increase in the level of activity of the cell relative to the reference level of activity in a miR-128 expressing cell that has not been contacted with the candidate compound indicates that the candidate compound is useful in the treatment or prevention of a pathology characterized by seizures.

In one embodiment, the miR-128 is provided in the form of miR-128 expressing cells, and in which the level of activity is determined by assaying for a level of expression of miR-128 in the cells. In another embodiment, the pathology characterized by seizures is selected from the group comprising epilepsy, status epilepticus, stroke, hypoxia, traumatic brain injury, infection, tumor, neurodegenerative disorders, metabolic and autoimmune disorders causing seizures.

One aspect of the present disclosure is a method of increasing miR-128 expression and/or activity in a mammalian cell, comprising administering an agent capable of increasing expression of miR-128 in the cell or mimicking the activity of miR-128 in the mammalian cell, wherein said agent comprises an oligomer of between 6 and 30 nucleotides in length, and wherein said oligomer comprises a contiguous nucleotide sequence which is identical to at least six contiguous nucleotides present in the sequence of miR-128. In one embodiment, the mammalian cell is selected from the group consisting of cells in the hippocampus, cortex, striatum and thalamus. In one embodiment, the method is performed in vitro. In another embodiment, the method is performed in vivo.

In one embodiment, the oligomer comprises a contiguous nucleotide sequence which is identical to the sequence of the seed region of miR-128. In another embodiment, the oligomer consists of a contiguous nucleotide sequence which is identical to the sequence of the seed region of miR-128. In one embodiment, the contiguous nucleotide sequence of the oligomer comprises between 7 and 23 nucleotides, which are identical to the sequence of the corresponding region of miR-128.

In one embodiment, miR-128 has the nucleotide sequence:

(SEQ ID NO: 1)
UCACAGUGAACCGGUCUCUUU.

One aspect of the present disclosure is directed to a method for treating or reducing the likelihood for the development of seizures and/or epilepsy in a subject, comprising administering miR-128 or an agent with 90 percent or more sequence homology to the corresponding region of miR-128 to a brain injury site in the subject. In one embodiment, miR-128 or an agent with 90 percent or more sequence homology to the corresponding region of miR-128 is administered intrathecally or intranasally and wherein the administration is to the hippocampus and/or the cortex. In one embodiment, miR-128 is encoded by a vector comprising a) promoter operatively linked to a nucleic acid molecule encoding miR-128; and b) a transcription termination sequence.

BRIEF DESCRIPTION OF THE FIGURES

FIGS. 18A-18C show some miRNA gene family members (mir-128 50 sequences).

DETAILED DESCRIPTION

Figures 1A, 1B, 1C:
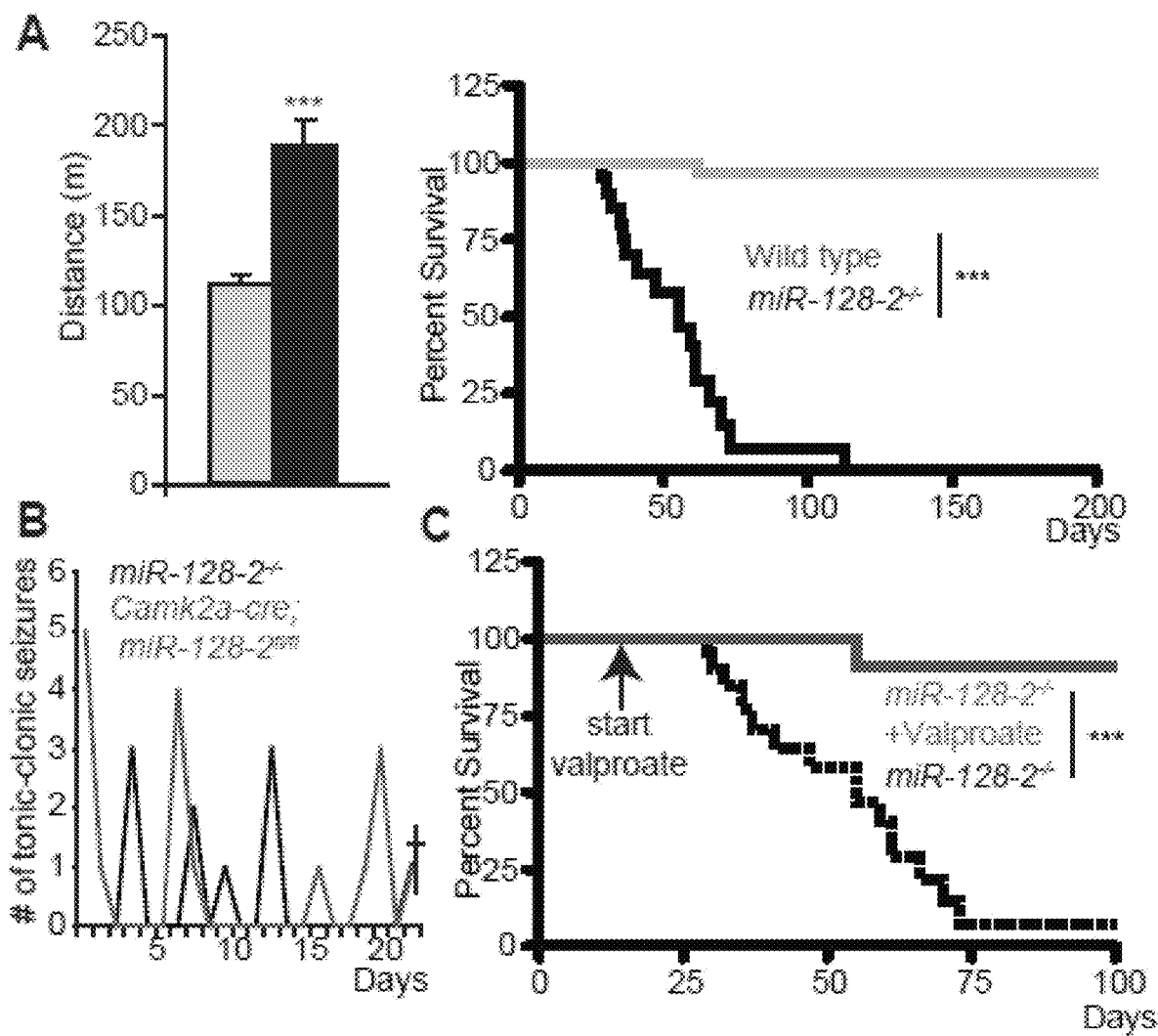
FIGS. 1A-1F show miR-128 controls motor behavior in mice. (A) Deficiency in miR-128-2 causes hyperactivity and premature death in mice. (Left panel) Motor activity was determined by measuring total horizontal distance in a 60 min open field assay (n=23 and 12). (Right panel) The lifespans of miR-128-2−/− mice and littermate controls are shown (n=20 and 46). (B, C) miR-128 deficiency causes fatal seizures that can be prevented by anti-convulsant treatment (B) Representative display of spontaneous tonic-clonic seizure episodes in miR-128-2−/− (black) or Camk2a-cre; miR-128-2fl/fl mice (red) during a 22-day observation period. (C) The lifespans of control miR-128-2-/- (dotted line, as shown in A) or sodium valproate-treated (red, n=11) miR-128-2-/- mice are shown (D) Deficiency in miR-128 in postnatal neurons causes hyperactivity and fatal epilepsy. Motor activity and survival rates of Camk2a-cre; miR-128-2fl/fl mice (n=21 and 25) and littermates (n=8 and 47) are shown. (E) Ectopic expression of miR-128 normalizes hyper-locomotion and prevents death of Camk2a-cre; miR-128-2fl/fl mice. Motor activity in Camk2a-cre; miR-128-2fl/fl; Rosa-miR-128 (n=4, blue) and wild-type mice (n=10, gray) are shown. The lifespans of Camk2a-cre; miR-128-2fl/fl mice in the presence (n=4, blue) or absence (n=9, black) of ectopic miR-128 expression are shown. (F) miR-128 deficiency in D1-neurons causes hyperactivity and fatal epilepsy. Motor activity (n=26 and 42) and lifespans (n=16 and 28) of mice with a D1-neuron specific miR-128 deficiency or control mice are shown. Error bars show s.e.m., Welch's t-test, non-significant (ns), $*p \leq 0.05$, $p \leq 0.01$, $*p \leq 0.001$. Kaplan-Meier graph shows survival curves of mutant and littermate control mice, $***p \leq 0.001$, log rank tests.

The invention relates to a therapeutic strategy to treat or reduce the likelihood of the development of seizure-related disorders and neurologic injuries. In particular, the invention relates to increasing the expression and/or activity of mircoRNA-128 in the brain of mammals to treat or reduce the likelihood of developing seizure-related disorders and neurologic injuries.

Epilepsy is a serious, chronic neurologic disorder characterized by recurrent spontaneous seizures which affects about 50 million people worldwide and the socioeconomic cost in Europe and the U.S. of epilepsy is thought to be about $30 billion per year. Anti-epileptic drugs typically control seizures in two-thirds of patients but generally do not alter the underlying pathophysiology. The remaining one-third of people with epilepsy are either drug-resistant or suffer unacceptable side effects from currently available drugs and continue to have seizures, leaving patients with few options, for example, brain surgery to remove part of the brain causing the seizures.

Epilepsy is the occurrence of sporadic electrical storms in the brain commonly called seizures. These storms cause behavioral manifestations (such as staring) and/or involuntary movements (such as grand mal seizures). There are several types of epilepsy, each with different causes, symptoms, and treatments. There are four main types of epilepsy, 1) generalized, 2) partial, 3) nonepilpetic and 4) status epilepticus.

1) Generalized seizures affect both cerebral hemispheres (sides of the brain) from the beginning of the seizure. They produce loss of consciousness, either briefly or for a longer period of time, and are sub-categorized into several major types: generalized tonic clonic; myoclonic; absence; and atonic. 2) In partial seizures the electrical disturbance is limited to a specific area of one cerebral hemisphere (side of the brain). Partial seizures are subdivided into simple partial seizures (in which consciousness is retained); and complex partial seizures (in which consciousness is impaired or lost). Partial seizures may spread to cause a generalized seizure, in which case the classification category is partial seizures secondarily generalized. Partial seizures are the most common type of seizure experienced by people with epilepsy. Virtually any movement, sensory, or emotional symptom can occur as part of a partial seizure, including complex visual or auditory hallucinations. 3) Nonepileptic seizures are episodes that briefly change a person's behavior and often look like epileptic seizures. Epileptic seizures are caused by abnormal electrical changes in the brain and, in particular, the cortex (brain's outer layer). Nonepileptic seizures are not caused by electrical disruptions in the brain. 4) Most seizures end after a few moments or a few minutes. If seizures are prolonged, or occur in a series, there is an increased risk of status epilepticus, a continuous state of seizure.

The development of symptomatic (acquired) epilepsy is thought to involve altered expression of ion channels and neurotransmitter receptors, synaptic remodelling, inflammation, gliosis and neuronal death, among others. However, few anti-epileptogenic interventions targeting these processes have shown sufficient efficacy in vivo, and our understanding of the cell and molecular mechanisms remains incomplete. There is currently no prophylactic treatment following a brain injury that causes epilepsy, or specific neuroprotective treatments for status epilepticus, or for acute neurologic injuries likely to cause brain damage or epilepsy, for example, stroke, trauma.

Febrile epilepsy has a high incidence rate of approximately 8% in infants. A main symptom of febrile seizure is known as a continuation of generalized convulsions for 1 to 5 minutes while suffering a fever at or over 38° C. Most cases of febrile seizure that have an onset of between 6 months after birth and around 5 years old cure by the time when the patient turns 6 years old. However, among patients whose onset of febrile seizure was under the age of one, there are some patients who suffer from convulsions continuously even after turning 6 years old, and there are some patients who are patients of Dravet syndrome, which are patients of an intractable epilepsy disease.

Severe Myoclonic Epilepsy of Infancy (SMEI), or now known as Dravet Syndrome, is a rare and catastrophic form of intractable epilepsy that begins in infancy. See general information at the url: www.dravetfoundation.org. The characteristics of intractable epilepsy associated with Dravet Syndrome include 1) high occurrence of partial seizure followed by a generalized seizure (particularly temporal lobe epilepsy); 2) high occurrence of symptomatic epilepsy caused by an organic lesion in the brain; 3) long-term absence of treatment from the onset to consultation of a specialist and high occurrence of seizures; and 4) high occurrence of status epilepticus in the anamnesis. In other words, the temporal lobe is likely to be a portion of the brain responsible for intractable epilepsy.

It is indicated that epilepsy becomes more intractable by changing of the nature thereof and evolving as acquired seizures are repeated. Seizures associated with intractable epilepsy are categorized into a variety of types, e.g., tonic seizures, tonic-clonic seizures, atypical absence seizures, atonic seizures, myoclonic seizures, clonic seizures, simple partial seizures, complex partial seizures, and secondary generalized seizures.

As such, Dravet Syndrome, a severe form of epilepsy, is a debilitating condition that generally affects babies and children. It is caused by mutations in the sodium channel Scn1a and children with the disease suffer from frequent, prolonged tonic clonic seizures and sudden unexplained death at young age. Despite the existence of numerous potent anti-seizure medications, more than 30% of epilepsy patients, especially patients diagnosed with Dravet Syndrome, do not respond to any treatment and are frequently resistant against all known FDA approved anti-seizure medications.

In this context, the inventors of the instant application have surprisingly discovered that the increased expression of a single brain-enriched microRNA, miR-128 that is conserved in mice and humans, can be used to control pathological neuronal excitability, seizures and epilepsy in vivo.

Accordingly, in one aspect, the present disclosure is directed to a method for treating or reducing the likelihood of the development of epilepsy or status epilepticus in an individual. The method comprises administering to an individual in need of such treatment (the subject) a therapeutically effective amount of an agent capable of increasing the expression and/or activity of MiR-128.

As well as applying for all epilepsy patients, this novel treatment may provide a lifeline especially to those patients suffering from epilepsy for whom there is no currently available treatment; that is, for about a third of patients suffering from epilepsy. For example, in the context of the present disclosure, the individual may be a patient diagnosed with Dravet Syndrome. Since the therapeutic agent of the present disclosure works on the central nervous system, the route of administration of the agent may include intrathecally or intranasally. The inventors identify the hippocampus and/or cortex to be particularly good targets for the therapeutic agent, and as such means for administering the agent such that the agent is most concentrated or exposed to the hippocampus and/or cortex is preferred.

In 2001, a large group of microRNAs (miRNAs) were isolated and identified. miRNAs are molecules that can regulate gene expression and interrupt translation through precise or imprecise base-pairing with their targets. It has become clear that non-coding RNA genes produce functional RNA molecules with important roles in regulation of gene expression, developmental timing, viral surveillance, and immunity. Not only the classic transfer RNAs (tRNAs) and ribosomal RNAs (rRNAs), but also small nuclear RNAs (snRNAs), small nucleolar RNAs (snoRNAs), small interfering RNAs (siRNAs), tiny non-coding RNAs (tncRNAs), repeat-associated small interfering RNAs (rasiRNAs) and microRNAs (miRNAs) are now believed to act in diverse cellular processes such as chromosome maintenance, gene imprinting, pre-mRNA splicing, guiding RNA modifications, transcriptional regulation, and the control of mRNA translation (Kawasaki and Taira, Nature, 2003, 423, 838-842).

MicroRNAs (miRNAs) are derived from endogenous genes that are initially transcribed as longer RNA transcripts. miRNAs are small, generally between 18 and 24 residues, polyribonucleotides derived from longer hairpin noncoding transcripts in eukaryotes. miRNAs play a significant role in cellular developmental and differentiation pathways. Consequently, there have been considerable efforts made to understand and characterize the temporal, spatial and cellular expression levels and patterns of expression of miRNAs to ascertain their precise role in cellular development and differentiation in both normal and disease states.

Figures 4A, 4B:
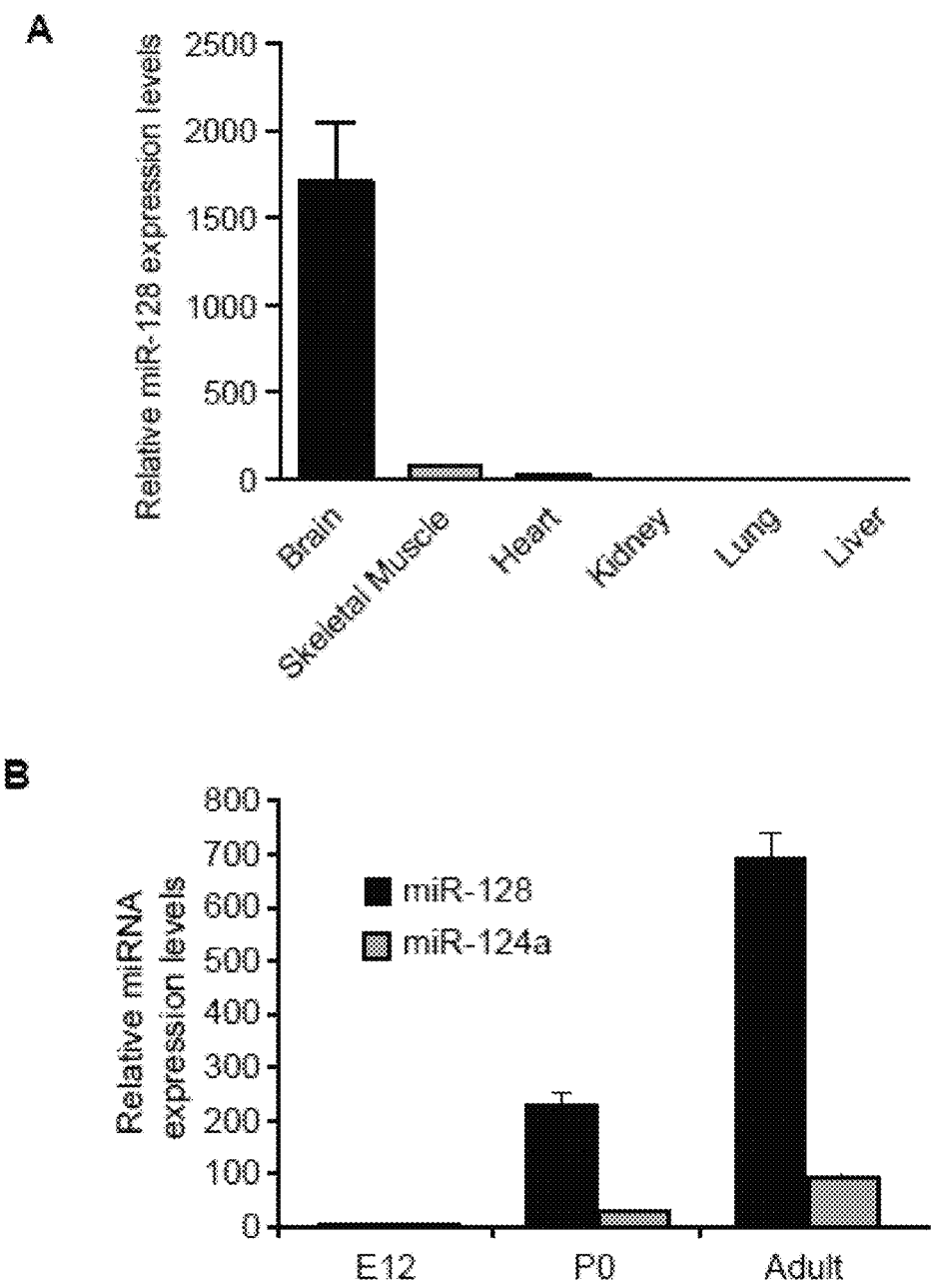
FIGS. 4A-4C show miR-128 is highly expressed in the postnatal mouse brain. (A) miR-128 is enriched in the mouse brain. Expression levels of miR-128 were measured by qRT-PCR in RNA purified from the brain, skeletal muscle, heart, kidney, lung, and liver of 8-week old adult mice (n=3). The expression levels of miR-128 were normalized to snoRNA135 expression and displayed as fold increase over respective miRNA expression levels in the liver. 1-way ANOVA followed by Turkey's posttest, p<0.01 for brain vs. other organ comparisons. (B) Postnatal brain development is accompanied by increase in miR-128 expression levels. Expression levels of miR-128 and the neuron-enriched miR-124a were measured by qRT-PCR in the brain derived from mouse embryos at day 12 of embryonic development (E12), newborn mice (PO) or 8-week old adult mice (n=3 per age group). The expression levels of miRNAs were normalized to snoRNA135 expression and displayed as fold increase over respective miRNA expression levels in the E12 embryonic brain. (C) miR-128 is expressed in different brain regions. Expression of miR-128 in indicated brain regions in adult mice was quantified as in (A) and shown relative to mean miR-128 expression in the brain stem (n=3 per region). Error bars show s.e.m.

Of the hundreds of microRNAs present, the inventors here have discovered one, miR-128, to play a critical role in epilepsy. miR-128 is one of the most abundant and highest enriched miRNA in the adult mouse and human brain (see for e.g., He et al., Neuron 73, 35, Jan. 12, 2012); and (FIG. 4A). The expression of miR-128 in the mouse brain increases gradually during postnatal development and peaks in adulthood (Miska et al., *Genome biology* 5, R68 (2004); and Krichevsky et al., *RNA* 9, 1274 (October, 2003)); and (FIG. 4B). miR-128's expression in diverse brain regions (FIG. 4D) suggested to the inventors of the instant application that miR-128 plays an important role in processes that are common to many neuronal cell-types.

The present invention relates to nucleic acids that perform the activities of endogenous miRNAs when introduced into cells. These nucleic acids are synthetic miRNA in some embodiments. Methods for introducing and removing miR- NAs from cells have been described (Meister et al., 2004; Hutvagner et al., 2004). Another publication describes the use of plasmids that are transcribed by endogenous RNA polymerases and yield specific miRNAs when transfected into cells (Zeng et al., 2002).

The inventors of the instant application discovered that microRNA-128 (miR-128), which is expressed in adult neurons, regulates motor behavior by modulating neuronal signaling networks and excitability. The inventors discovered that miR-128 governs motor activity by suppressing the expression of various ion channels and signaling components of the extracellular signal-regulated kinase ERK2 network that regulate neuronal excitability. Accordingly, miR-128 has been discovered here to be a novel therapeutic agent for treating epilepsy and related conditions, including treatment-resistant epilepsy in Dravet-syndrome.

In particular, one aspect of the present disclosure is directed to a method for treating or reducing the likelihood of the development of epilepsy in an individual in need of such treatment. The method comprises administering to the individual a therapeutically effective amount of an agent capable of increasing the expression and/or activity of MiR-128, wherein said individual has suffered a prior brain injury that increases said individual's risk of epilepsy. The prior brain injury may have been caused by stroke.

The therapeutic agent may miR-128, an agent with 90 percent or more sequence homology to miR-128, or an inducer of miR-128 activity and/or expression, for example, brain-derived neurotrophic factor (BDNF). The agent capable of increasing and/or activating miR-128 may be chemically stabilized miR-128, a nucleic acid encoding miR-128, and/or a viral vector encoding miR-128. One of the advantages of miR-128 as a treatment for epilepsy is its ability to target several genes within a signaling network regulating neuronal excitability.

The control of motor behavior in animals and humans requires constant adaptation of neuronal networks to signals of various types and strengths. In mice, a reduction of miR-128 expression in postnatal neurons was shown to increase motor activity and fatal epilepsy. Overexpression of miR-128 was shown to attenuate neuronal responsiveness, suppress motor activity and alleviate motor abnormalities associated with Parkinson's-like disease and seizures.

Accordingly, one aspect of the present disclosure is directed to a method for treating or reducing the likelihood of the development or occurrence of seizures. The method comprises administering to an individual in need of such treatment a therapeutically effective amount of an agent capable of increasing the expression and/or activity of MiR-128, wherein said patient has a brain-related disorder characterized by development of seizures. The brain-related disorder characterized by development of seizures may be stroke, hypoxia, traumatic brain injury, infection, tumor, neurodegenerative disorders, metabolic and/or autoimmune disorders causing seizures. The individual may be someone diagnosed with Dravet Syndrome.

The subject may be of any age. The agent may be administered intrathecally or intranasally. The goal of the administration is to allow for the therapeutic agent to reach its target in the central nervous system. For example, preferably, the agent is administered such that it contacts the hippocampus and/or cortex. It stands noted that miR-128 was shown not affect brain morphology, striatal morphology, or neuronal survival.

Various delivery systems are known and can be used to administer a therapeutic of the invention, e.g., intra-nasally. Methods of introduction include but are not limited to intranasal, epidural, and intracerebral. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. In addition, the compositions of the invention can be administered into the central nervous system by any suitable route, including intraventricular and intrathecal injection; intraventricular injection may be facilitated by an intraventricular catheter, for example, attached to a reservoir, such as an Ommaya reservoir.

Preferably, the therapeutic is delivered to the central nervous system. Delivery means include intrathecal delivery, and inhalation delivery. Methods for achieving these means of delivery will be well known to those skilled in the art of drug delivery, and include, for example, intrathecal delivery by mini-osmotic pumps, or by means of an implant (eg small silicon implant) that will release the active agent. Such implants can, for example, be used to administer miR-128 or an agent with 90 percent or more sequence homology to miR-128 over a period of time, such that the severity and/or frequency of epilepsy episodes and associated seizures are reduced. The therapeutic agent is delivered such that the agent comes into contact with cells in the hippocampus and/or cortex, preferably without being more widely distributed Another aspect of the present disclosure is directed to a method of identifying compounds useful in the treatment or reducing the likelihood of a pathology characterized by seizures. The compounds may be identified by contacting a miR-128-expressing cell with a candidate compound, and determining the level of expression and/or activity of the miR-128 in the cell. An increase in the level of expression and/or activity of miR-128 relative to the reference level of activity of miR-128 in a miR-128-expressing cell that has not been contacted with the candidate compound indicates that the candidate compound is useful in the treatment or prevention of a pathology characterized by seizures.

In one embodiment, the miR-128 may be provided in the form of miR-128 expressing cells. The pathology characterized by seizures may be epilepsy, status epilepticus, stroke, hypoxia, traumatic brain injury, infection, tumor, neurodegenerative disorders, metabolic and/or autoimmune disorders causing seizures.

The term human "miR-128" should also be taken to include any human miR-128 paralogues. The miRNA gene family includes many members. Some miRNA gene family members (mir-128 50 sequences) are shown in FIGS. 18A-18C.

Figure 5A:
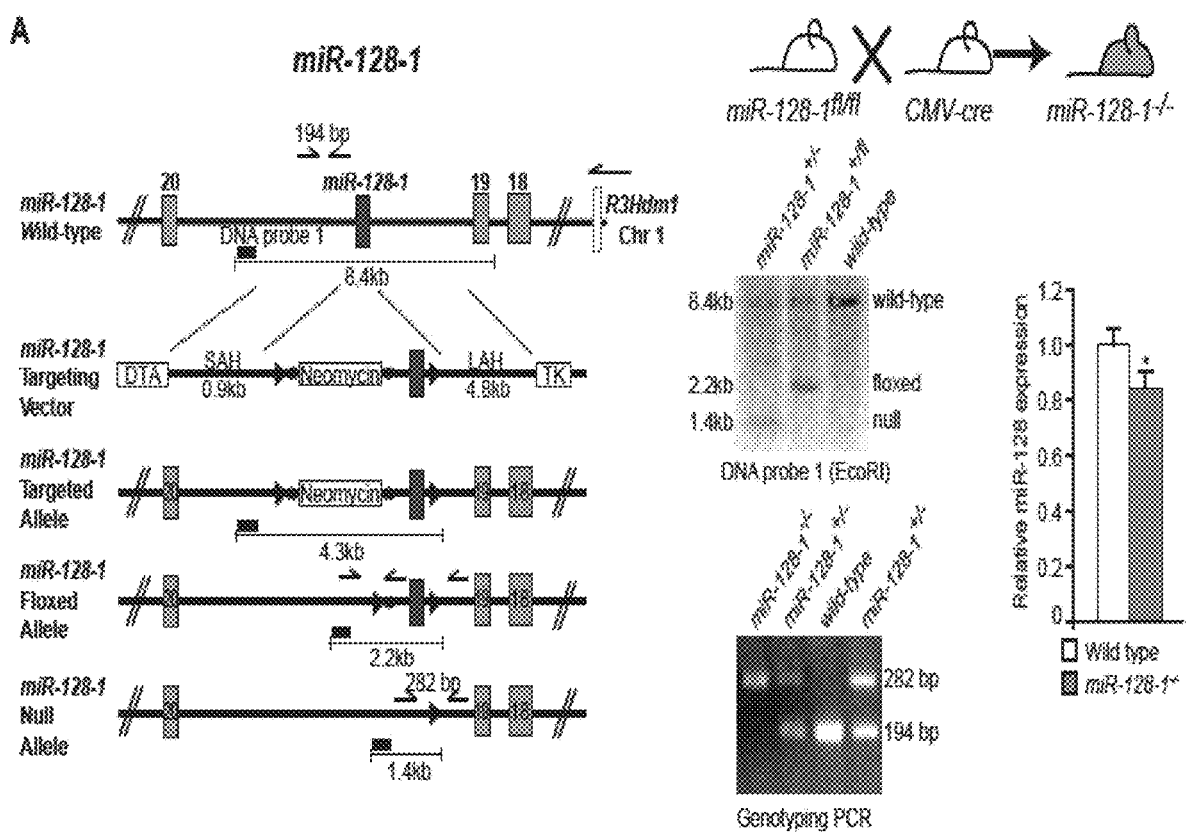
FIGS. 5A-5D show miR-128-1 and miR-128-2 genes contribute differentially to miR-128 expression in the brain. (A, B) Generation of the (A) miR-128-1 and (B) miR-128-2 loci for conditional gene inactivation in mice. (Left panels) The strategy for gene modification and inactivation of miR-128 genes are shown. The regions containing the miRNA hairpin in both of the miR-128 carrying genes were flanked with loxP sites in mouse ES cells followed by routine procedure for generation of miR-128-1fl/fl and miR-128-2fl/fl mice. MicroRNA hairpin, filled rectangle; exons, open rectangles; loxP sites, black triangles. Neomycin resistance gene flanked by FRT sequences (black circles) was removed from targeted loci by using FLT recombinase; DTA, diphtheria toxin gene; TK, thymidine kinase gene; LAH/SAH, long and short arm of homology. (Right panels) miR-128-1 (miR-128-1-/-) or miR-128-2 (miR-128-2-/-) deficient mice were generated by breeding miR-128-1fl/fl and miR-128-2fl/fl mice, respectively, to CMV-cre mice. Modified miR-128-1 and miR-128-2 alleles were identified by Southern blotting of the mouse tail DNA digested with EcoRI or SacI using the indicated DNA probes (black rectangles) or by PCR genotyping using primers as indicated in the scheme. The relative expression levels of miR-128 in the striatum of mice deficient for the miR-128-1 (n=7 each) or miR-128-2 (n=5 and 3) gene are shown. (C) Inactivation of the miR-128-1 gene does not affect motor activity or survival in mice. The impact of miR-128-1 deficiency on motor activity in mice was measured by using open field analysis. (Left panel) Total horizontal distance moved in meters and (middle panel) the number of vertical rearing episodes within 60 min in the open field are shown (n=7 and 9). (Right panel) The life spans of mice deficient for miR-128-1 (n=6) and their respective wild-type littermate controls (n=22) are shown. (D) Inactivation of the miR-128-2 gene increases exploration in mice. The numbers of vertical rearing episodes of or miR-128-2−/− and littermate controls are shown (n=23 and 12). Error bars show s.e.m., *p≤0.05, **p≤0.01, Welch's t-test and log-rank test.
Figure 5B:
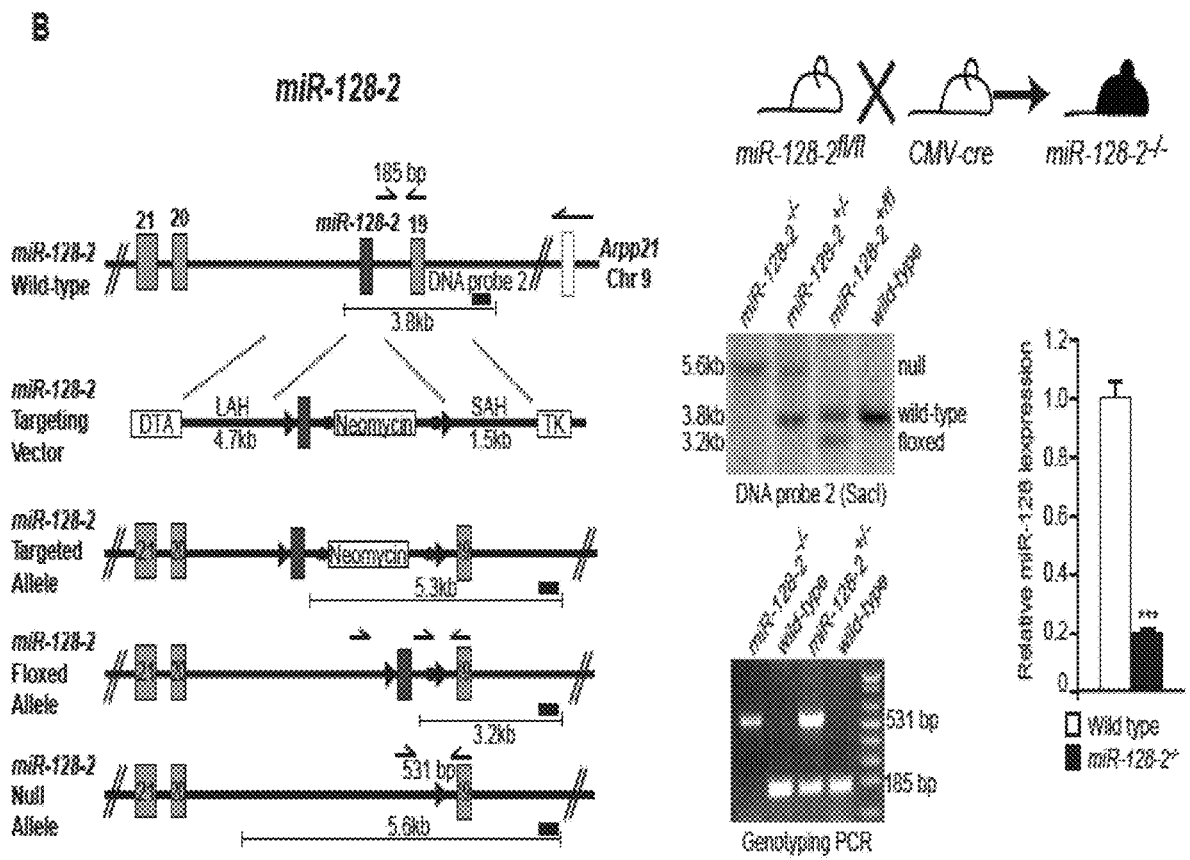

In the present disclosure, the inventors of the instant invention surmised that there is a potent regulatory role for miR-128 in brain function from their seminal observation that there is early-onset fatal epilepsy in mice deficient in miR-128 (FIG. 1A).

miR-128 is encoded by two separate genes, miR-128-1 and miR-128-2, on mouse chromosomes 1 and 9 (FIG. 5A, B) or human chromosomes 2 and 3, respectively. In mice, germline miR-128-2 deficiency was shown to result in an 80% reduction of miR-128 expression in the forebrain, whereas ablation of the miR-128-1 gene eliminated only 20% of miR-128 (FIG. 5A, B).

Figure 5C:
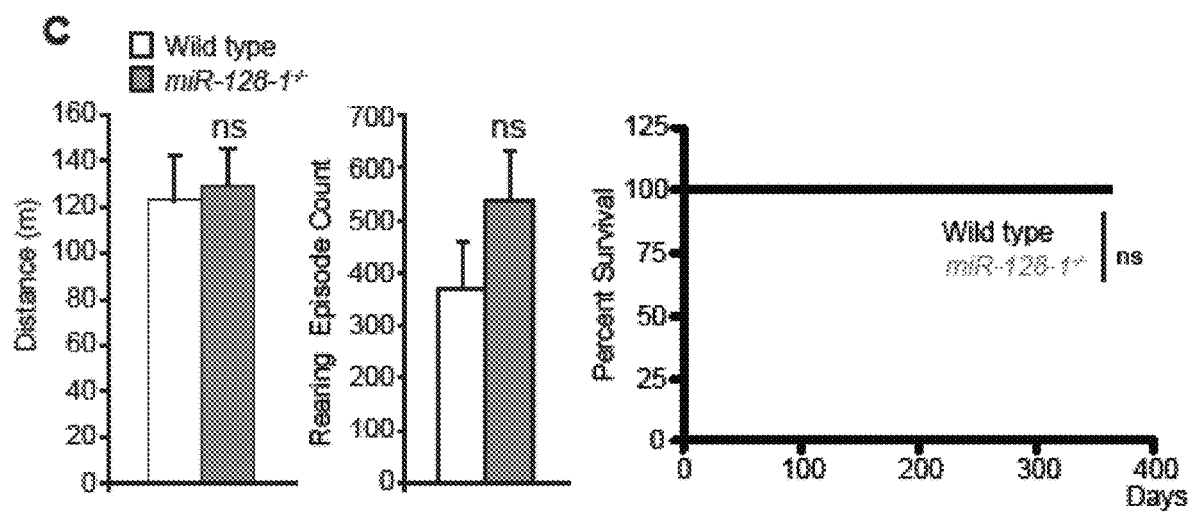
Figure 5D:
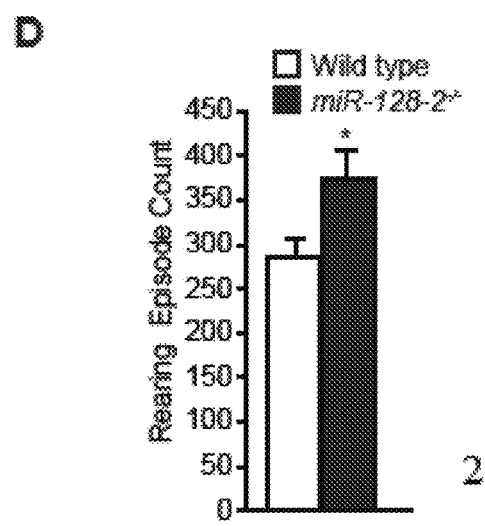

Applicants have discovered that the profound decline in miR-128 expression levels in miR-128-2−/− but not miR-128-1−/− mice is associated with the development of hyperactivity and increased exploration at 4 weeks of age (FIG. 1A, FIG. 5C, D). Here, the inventors show that the juvenile hyperactivity in miR-128-2-/- mice progressed quickly to severe seizures and death at 2-3 months of age (FIG. 1A, B). Further, the lethal impact of miR-128 deficiency in mice was shown to be prevented by treatment with the anticonvulsant drug valproic acid (FIG. 1C), thus demonstrating the causal role of seizures in the animals' death.

Figures 1D, 1E:
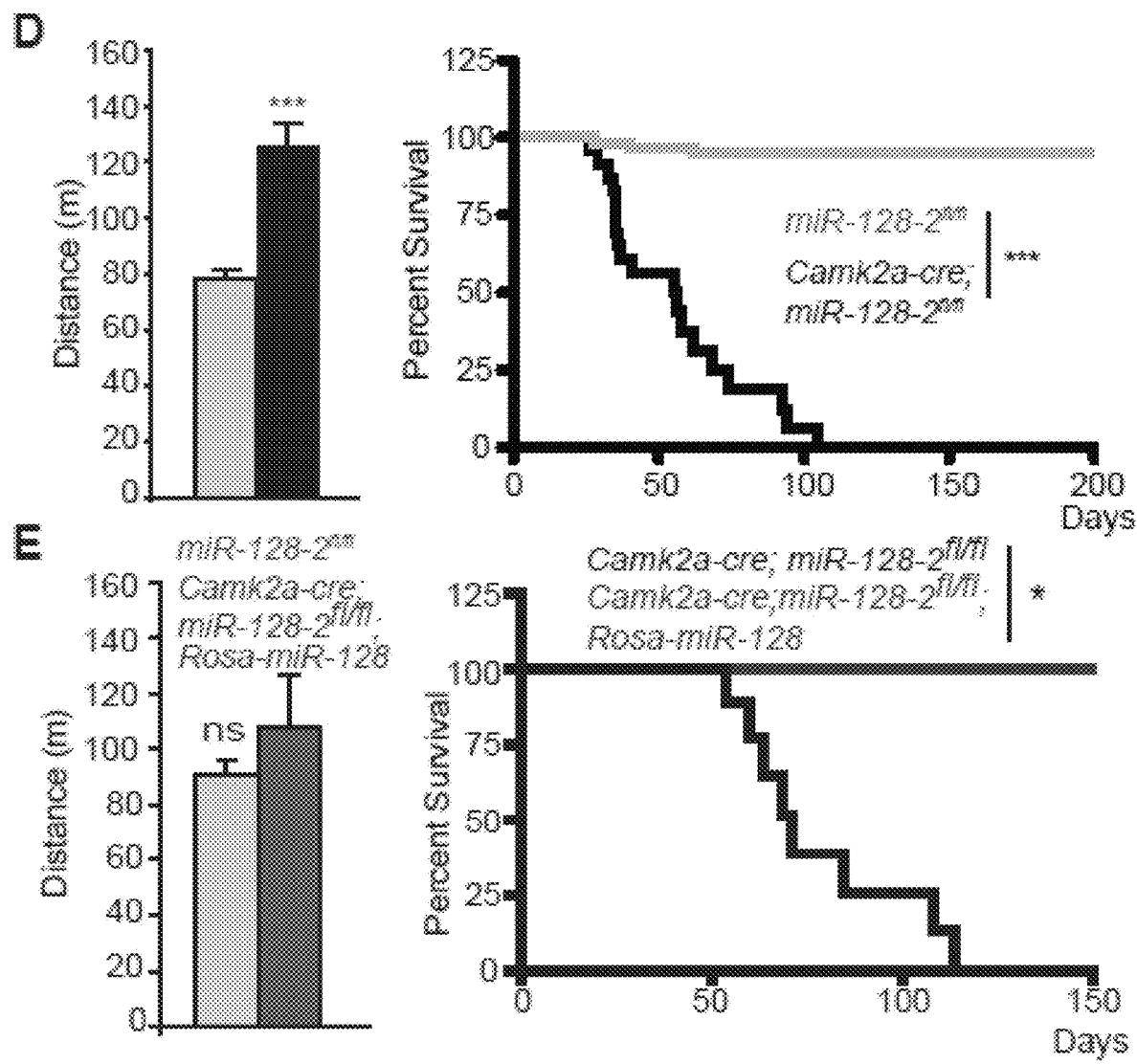
Figure 6A:
FIGS. 6A-6C show increased explorative activity in mice with conditional inactivation in postnatal Camk2a- and D1-, but not D2-neurons in mice. (A) miR-128 deficiency in postnatal Camk2a-neurons increases exploration. miR-128 deficiency in postnatal Camk2a-neurons has been achieved by breeding Camk2a-cre with miR-128-2fl/fl mice. (Left panel) The bar graph shows the relative miR-128 expression levels in Camk2a-cre; miR-128-2f/fl mice and control littermates (n=7 and 4). (Right panel) The number of vertical rearing episodes performed by Camk2a-cre; miR-128-2fl/fl mice and control littermates (n=21 and 8) are shown. (B) miR-128 deficiency in D1-neurons increases exploration. miR-128 deficiency in D1-neurons has been achieved by breeding Drd1a-cre with miR-128-2f/fl mice. Relative striatal miR-128 expression levels (left, n=3 each), and vertical rearing episodes (right) of Drd1a-cre; miR-128-2f/fl mice and control littermates (n=22 and 26) are shown. (C) miR-128 deficiency in D2-neurons does not affect motor activity or survival in mice. miR-128 deficiency in D2-neurons has been achieved by breeding A2A-cre with miR-128-2fl/fl mice. Striatal miR-128 expression levels (left, n=3 each), horizontal motor activity and vertical rearing episodes (middle, n=9 and 7), and survival span (right, n=8 and 7) of A2A-cre; miR-128-2fl/fl mice and respective littermates (n=7) are shown. Error bars show s.e.m., *p≤0.05, **p≤0.01, Welch's t-test and log-rank test.
Figure 6A:
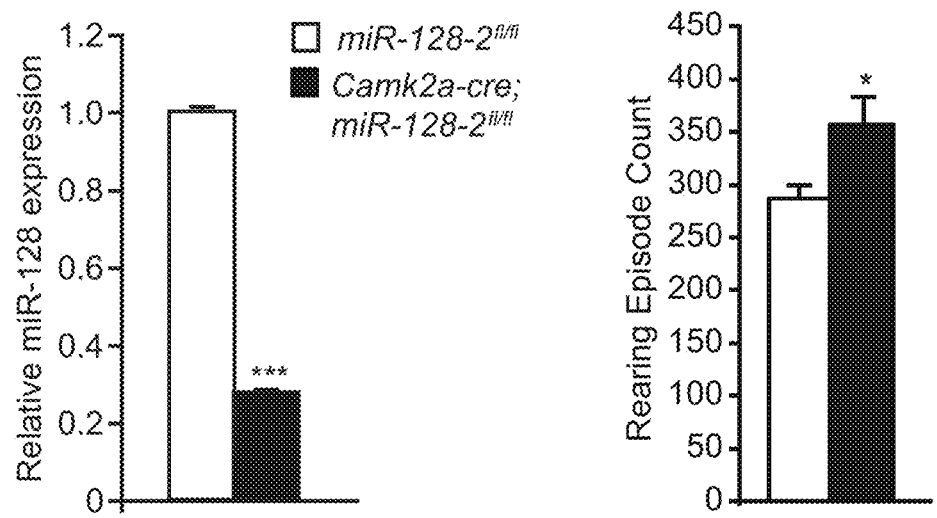
Figure 7A:
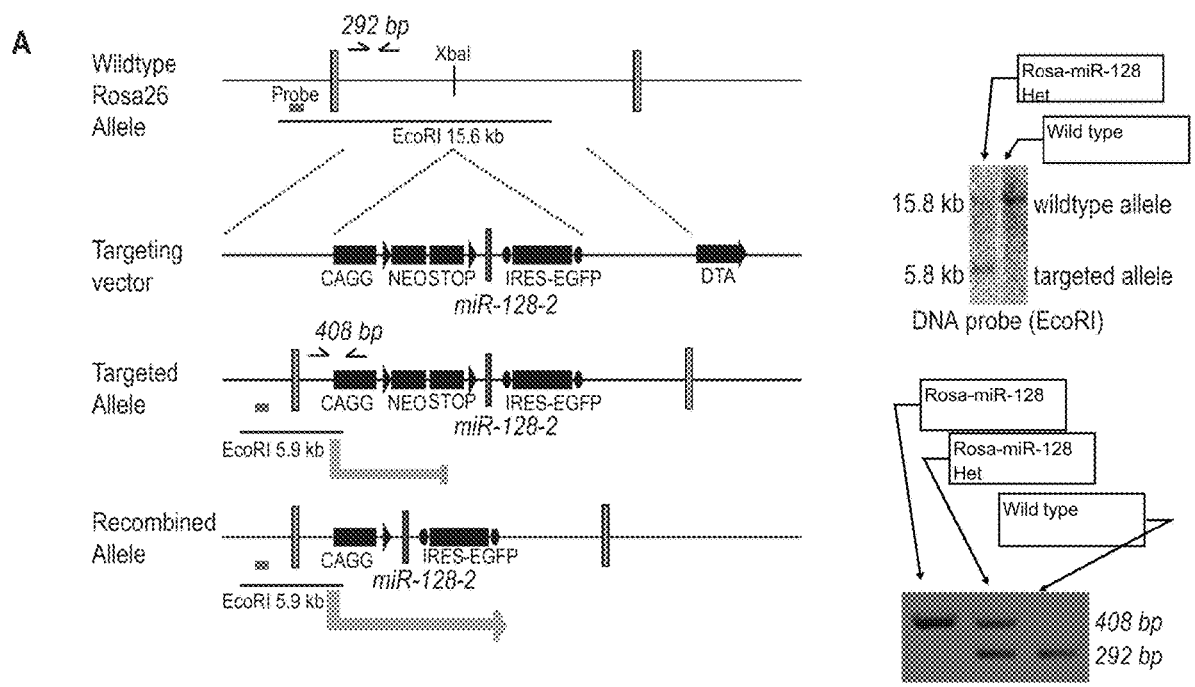
FIG. 7A-7C show ectopic expression of miR-128 in vivo attenuates motor activity in wild-type mice and normalizes miR-128 expression levels in Camk2a-cre; miR-128-2fl/fl mice. (A) Targeting strategy for the generation of mice with conditional overexpression of miR-128. The exogenous miR-128-2 gene was inserted into the endogenous Rosa26 gene locus in ES cells using a knock-in strategy as described previously. The miR-128-2 gene (red rectangle) was separated from a strong CAGG promoter by a floxed-STOP-Neomycin cassette. Exons, grey rectangles. DTA, diphtheria toxin gene. The modified ROSA-Stopf/fl-miR-128 allele (for simplification from now on called Rosa-miR-128) was confirmed by Southern blot analysis of the EcoRI digested DNA (top right) using the indicated DNA probe (blue rectangle) or by PCR genotyping (bottom right, primer locations as indicated in scheme). (B) Reduced motor activity and exploration in mice with neuron-specific overexpression of miR-128. (Top) Mice with postnatal neuron specific overexpression of miR-128 (Camk2a-cre; Rosa-miR-128) were generated by breeding Camk2a-cre with Rosa-miR-128 mice. (Left) miR-128 expression levels in the striatum were measured by qRT-PCR (n=3 each) as described (FIG. 4) and are shown relative to mean miR-128 expression in the wild type striatum. Welch's t-test. (Middle and right) Total horizontal distance and rearing activity in an open-field over 60 minutes for Camk2a-cre; Rosa-miR-128 mice (n=21) and littermate controls (wild type n=8, Camk2a-cre n=5, Rosa-miR-128 n=17) are shown. 1-way ANOVA followed by Turkey's post test. (C) Ectopic expression of miR-128 from the Rosa26 locus normalizes miR-128 expression levels in Camk2a-cre; miR-128-2fl/fl mice. (Left) Mice with postnatal neuron specific knock-out of miR-128-2 and ectopic expression of miR-128-2 from the Rosa26 locus (Camk2a-cre; miR-128-2f/fl; Rosa-miR-128) were generated by breeding Camk2a-cre; miR-128-2fl/fl to Rosa-miR-128 mice. (Right) miR-128 expression in the striatum of Camk2a-cre; miR-128-2f/fl; Rosa-miR-128 mice (n=4) was measured by qRT-PCR and data are shown relative to mean expression in littermate controls (n=3). Welch's t-test. Error bars show s.e.m., *p≤0.05, **p≤0.01.
Figure 7B:
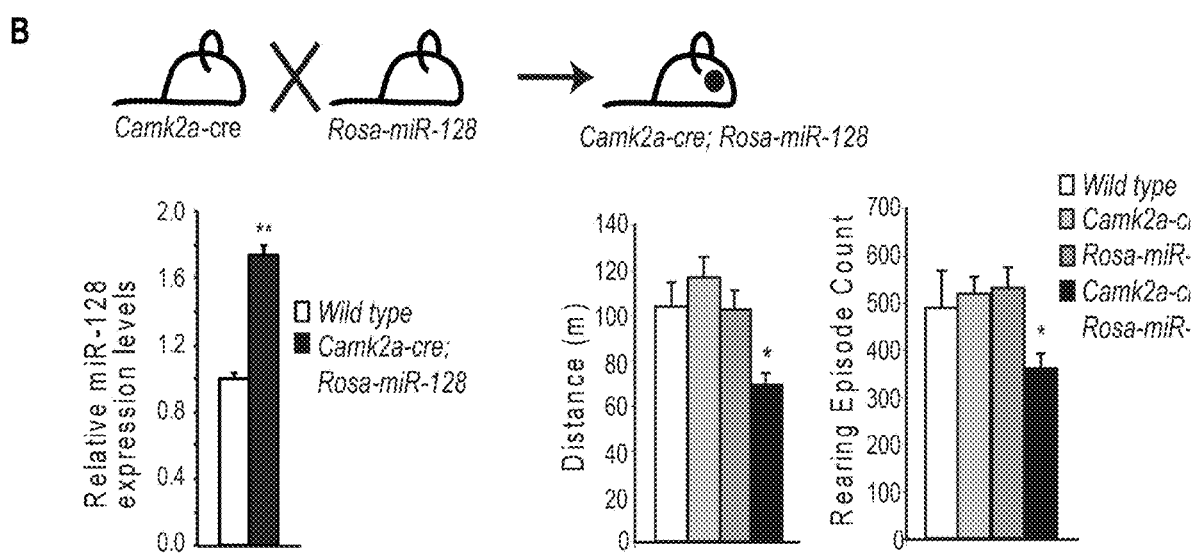
Figure 7C:
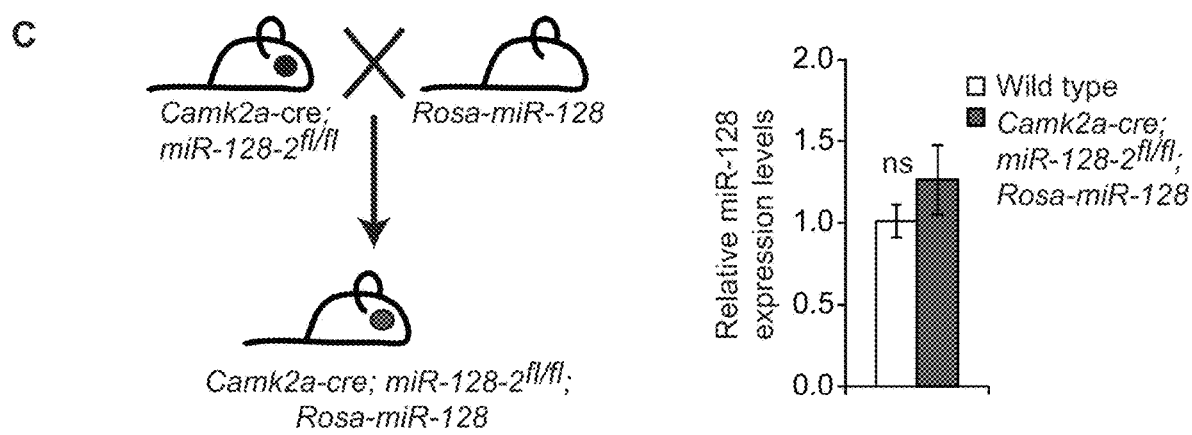

The observation of hyperactivity and fatal epilepsy in miR-128-2 deficient mice reflects the ability of miR-128 to control the excitability of postnatal neurons. Selective inactivation of the miR-128-2 gene in forebrain neurons (Camk2a-cre; miR-128-2fl/fl) lead to a reduction of miR-128 expression, followed by early onset hyperactivity, seizures, and death, as observed in miR-128-2-/- mice (FIG. 1B, D, FIG. 6A). Moreover, correction of miR-128 deficiency by ectopic miR-128-2 expression in neurons normalized motor activity and prevented the seizure-induced death (FIG. 1E, FIG. 7A, C).

The present data revealed that miR-128 has the ability to regulate seizure susceptibility in a dose-dependent fashion and protect against seizures regardless if they are caused by increased neuronal excitability (kainic acid model) or decreased inhibitory activity (picrotoxin model) of neurons.

In one aspect, the present disclosure relates to a pharmaceutical composition for use in treating or reducing the likelihood of the development of a neuronal pathology characterized by seizures comprising an agent capable of activating miR-128 in combination with a pharmaceutically acceptable excipient. In one embodiment of the present invention, the pathology characterized by seizures is selected from the group comprising epilepsy, status epilepticus, stroke, hypoxia, traumatic brain injury, infection, tumor, neurodegenerative disorders, metabolic and autoimmune disorders causing seizures. In a particular example, the neurologic disease is one associated seizures and/or epilepsy, and in particular, for example, Dravet syndrome. It is contemplated that any embodiment discussed in this specification can be implemented with respect to any method, kit, reagent, or composition of the invention, and vice versa. Furthermore, compositions of the invention can be used to achieve methods of the invention.

The inventors of the instant application sought to gain an understanding of the mechanism that mediates miR-128-dependent control of motor activity, and to avoid interference between phenotypes caused by the loss of miR-128 in diverse neuronal cell-types. A study was devised and performed, restricted to investigate the effect of miR-128-2 deficiency on dopamine responsive neurons that regulate motor behavior in mice and humans. There are two major dopamine responsive Camk2a-expressing neuron types in the mouse forebrain, which have distinct contributions to motor activity.

Figure 1F:
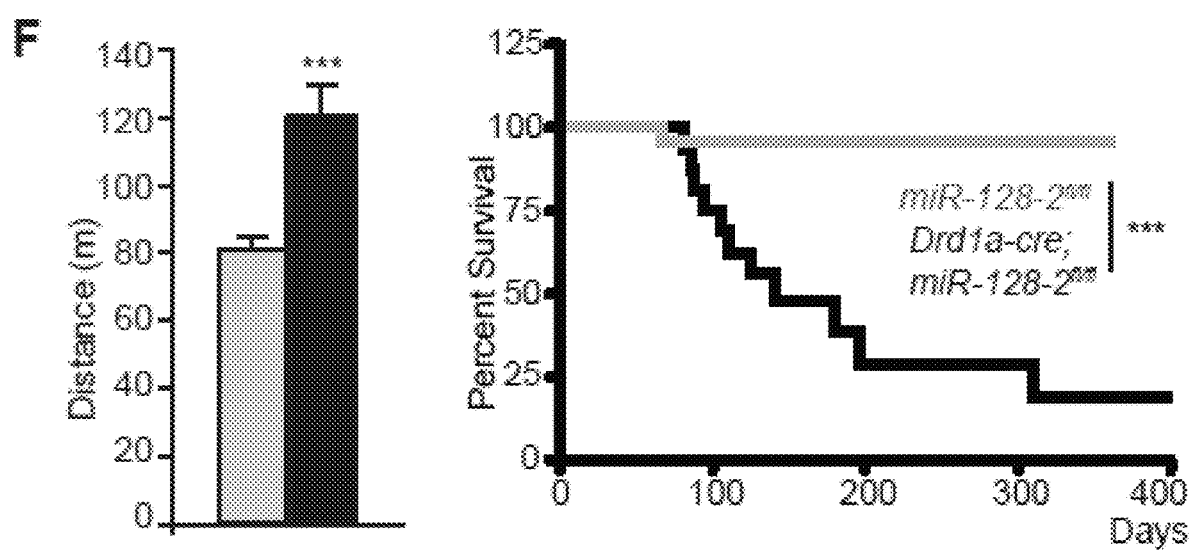
Figures 2A, 2B, 2C:
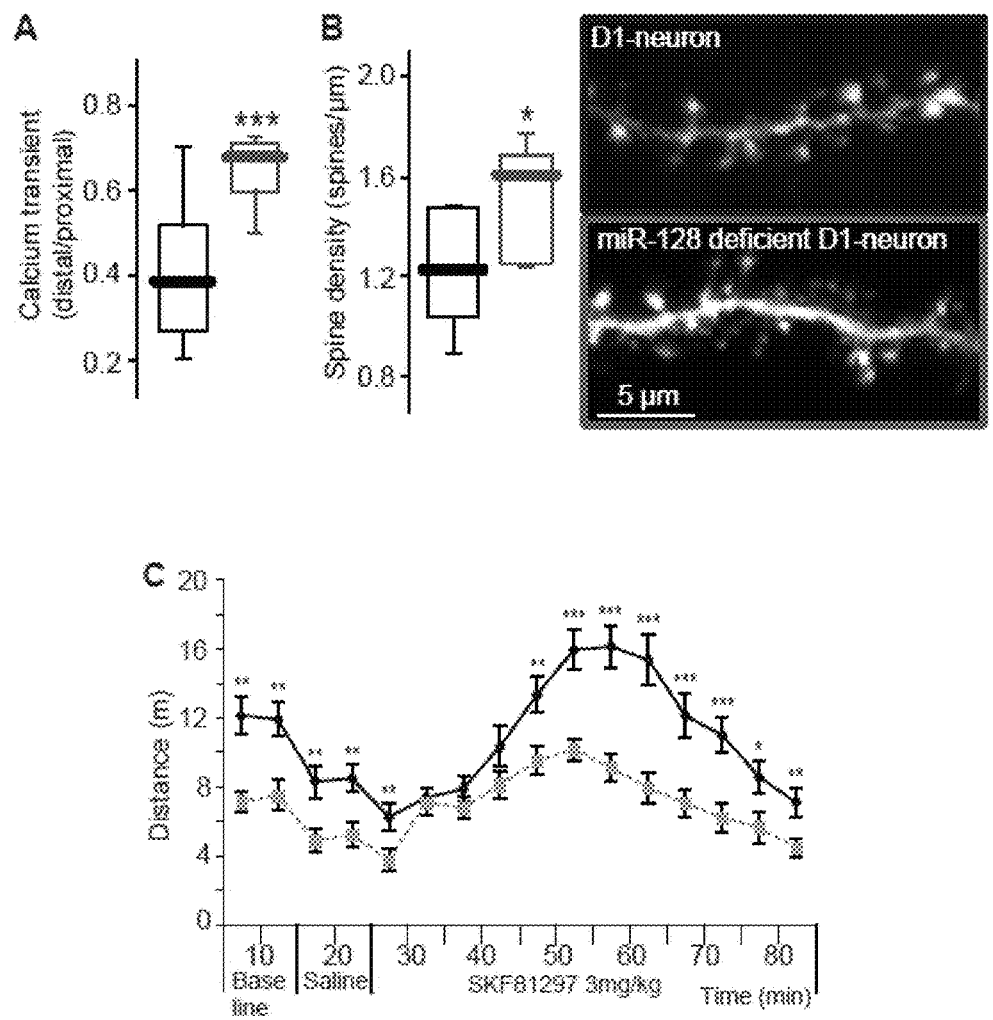
FIGS. 2A-2E show miR-128 controls D1-neuron excitability and responsiveness to dopamine. (A, B) miR-128 regulates D1-neuron dendritic excitability and number of spines. (A) Single action potentials were generated in the soma and action potential invasion was calculated by dividing the distal calcium signal by the maximum proximal calcium signal per cell (n=4 cells, 11-21 shafts per group). Mann-Whitney nonparametric test, $***p \leq 0.001$ (B) Representative maximum intensity projection images of distal dendrites in control and mutant D1-neurons are shown. Boxplots display population spine densities (n=10-11 cells per group). Mann-Whitney nonparametric test, error bars show 90th percentile interval, $*p \leq 0.05$. (C-E) miR-128 regulates motor response, ERK2 phosphorylation, and immediate early gene (IEG) induction upon dopamine D1 receptor (Drd1) activation in D1-neurons. (C) Motor activity of Drd1a-cre; miR-128-2fl/fl and control mice (n=25 and 30) was evaluated in an open-field chamber. Saline and 3 mg/kg Drd1 agonist SKF81297 were injected i.p. at 10 and 20 minute, respectively. (D) ERK2 phosphorylation was quantified by Western blotting of striatal lysates derived from Drd1a-cre; miR-128-2fl/fl and control mice that received saline or D1-agonist SKF81297 injection (n=5 each). Bar graph displays the ratio of phospho-ERK2 to total ERK2 expression. (E) IEG and D1-neuron-expressed Darpp32 gene expression levels were measured by qRT-PCR of D1-neuron specific polyribosome-associated mRNAs purified from saline or SKF81297 treated Drd1a-TRAP; Drd1a-cre; miR-128-2fl/fl and control mice (n=5 each). Error bars display s.e.m., Welch's t-test, $*p \leq 0.05$, $p \leq 0.01$, $*p \leq 0.001$.
Figure 2D:
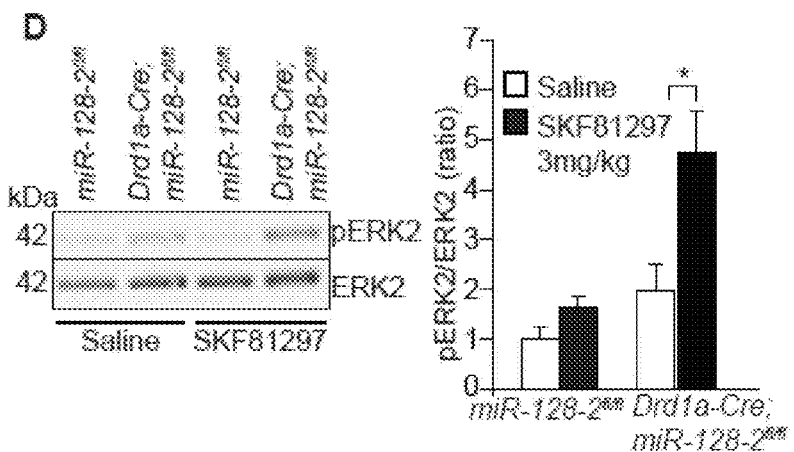
Figure 2E:
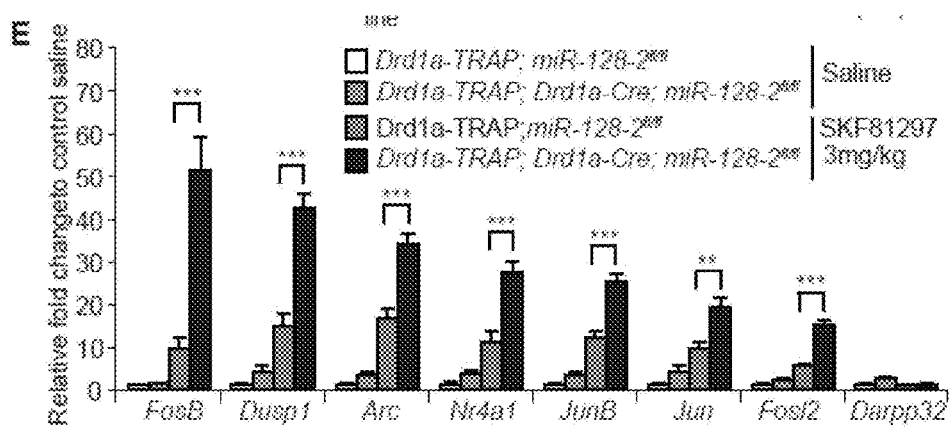
Figure 6B:
Figure 6B:
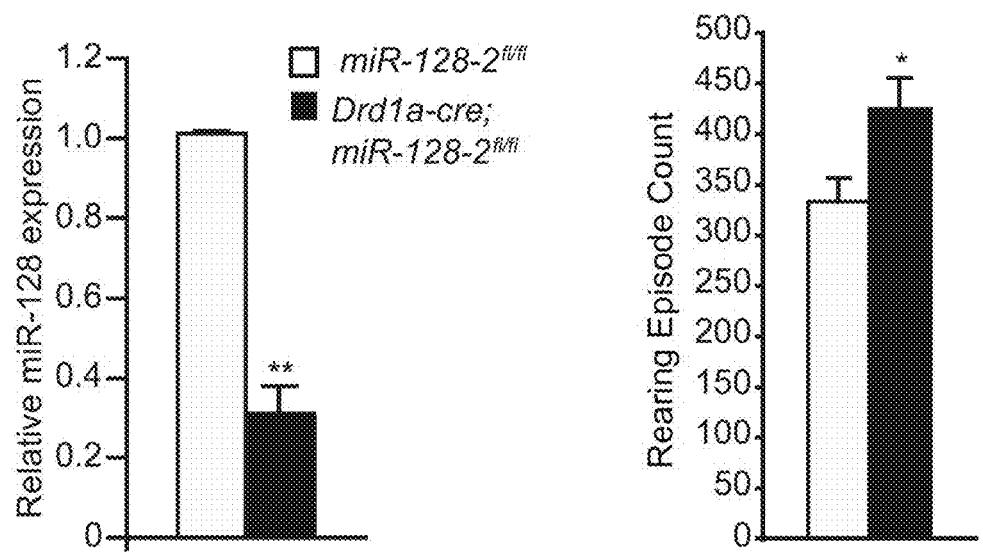
Figure 6C:
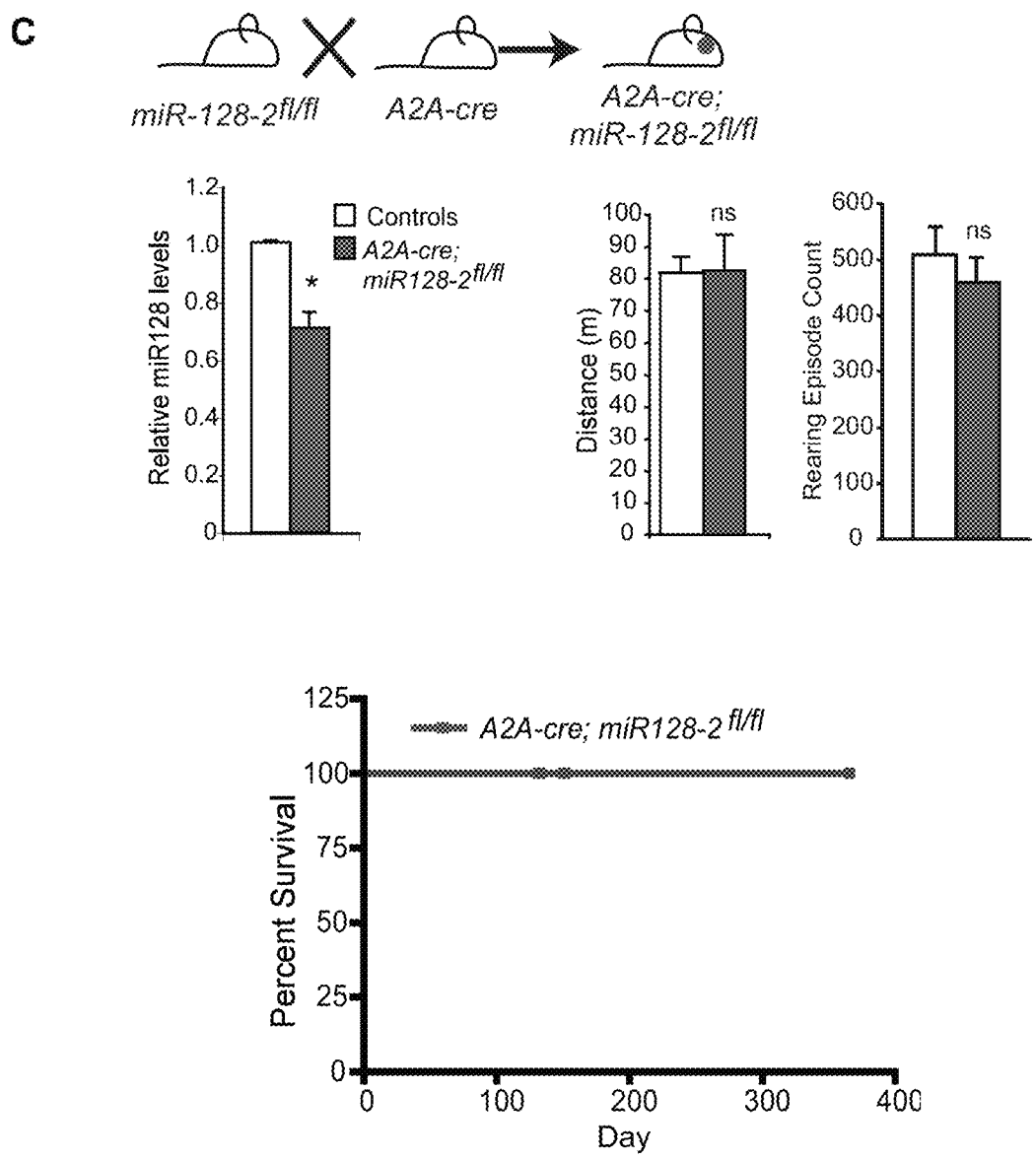

While activation of the dopamine 1 receptor expressing neurons (D1-neurons) increases locomotion, activation of dopamine 2 receptor expressing neurons (D2-neurons) reduces locomotion in mice. Applicants found that miR-128 deficiency in D1-neurons (Drd1a-cre; miR-128-2fl/fl), but not in D2-neurons (A2a-cre; miR-128-2fl/fl), lead to juvenile hyperactivity followed by lethal seizures at around 5 months of age (FIG. 1F, FIG. 6B, C).

As such, one aspect of the present disclosure is a method of activating miR-128 in a mammalian cell, comprising administering an agent capable of activating or mimicking the activity of miR-128 to the mammalian cell, wherein said agent comprises an oligomer of between 6 and 30 nucleotides in length, and wherein said oligomer comprises a contiguous nucleotide sequence which is fully complementary to at least six contiguous nucleotides present in the sequence of miR-128. The mammalian cells that may be used include cells from the hippocampus, cortex, striatum, and/or a thalamus, IPSC-derived neurons, and various cell-lines. The method may be performed in vitro or in vivo.

The oligomer may comprise a contiguous nucleotide sequence which is either identical to or is fully complementary to the sequence of the seed region of miR-128. The oligomer may consist of a contiguous nucleotide sequence which is either identical to or is fully complementary to the sequence of the seed region of miR-128. The contiguous nucleotide sequence of the oligomer may comprise between 7 and 23 nucleotides, which are fully complementary to the sequence of the corresponding region of miR-128.

Figure 3A:
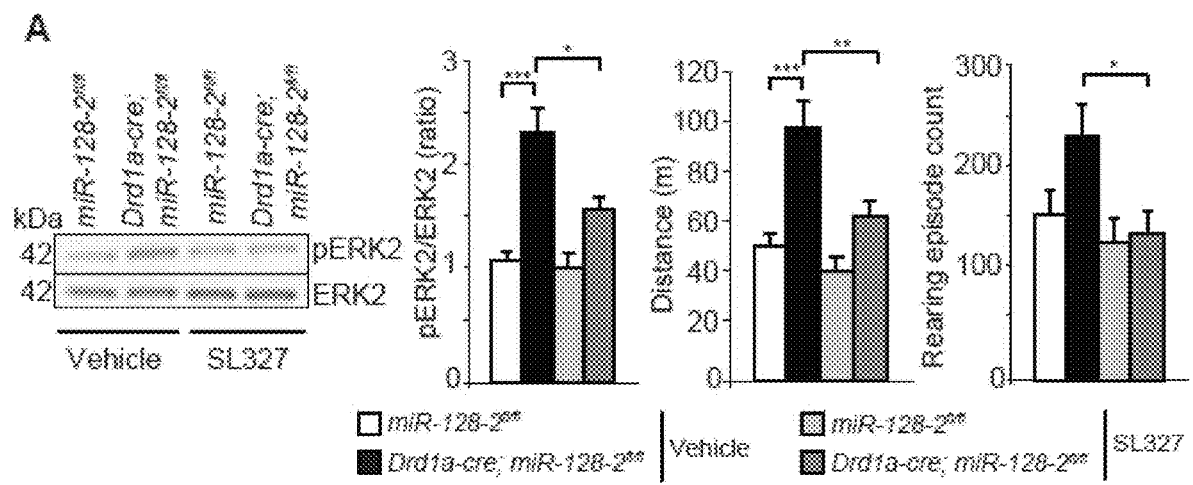
FIGS. 3A-3C show abnormal motor activity caused by miR-128 deficiency is corrected by pharmacological ERK inhibition or ectopic miR-128 expression. (A) Drd1a-cre; miR-128-2fl/fl and littermate control mice were injected i.p. with either vehicle or 12 mg/kg of the MEK1 inhibitor SL327 (n=5/group). Western blot analysis of ERK2 phosphorylation at 30 min after drug injection (left) and motor activity following vehicle or SL327 injection (right) are shown. 2-way ANOVA followed by Bonferroni post-test. Error bars show s.e.m., $*p \leq 0.05$, $p \leq 0.01$, $*p \leq 0.001$. (B) Overexpression of miR-128 suppresses D1-neuron hyper-responsiveness in the dopamine-depleted striatum. The number of contralateral rotations at baseline and in response to cocaine (10 mg/kg) or D1-agonist SKF81297 (5 mg/kg) in unilateral 6-OHDA lesioned Camk2a-cre; Rosa-miR-128 or control mice (n=11/group) are shown. Error bars show s.e.m., Welch's t-test, $**p \leq 0.01$. (C) miR-128 reduces the susceptibility to chemically-induced seizures in mice. The numbers of Camk2a-cre; Rosa-miR-128 or littermate control mice (n=12/group) that exhibit tonic-clonic seizures 60 minutes after i.p. injection of pro-convulsive drugs kainic acid (30 mg/kg, p-value=0.005) or picrotoxin (3 mg/kg, p-value=0.04) are shown. p-values were calculated by Fisher's exact test.
Figures 3B, 3C:
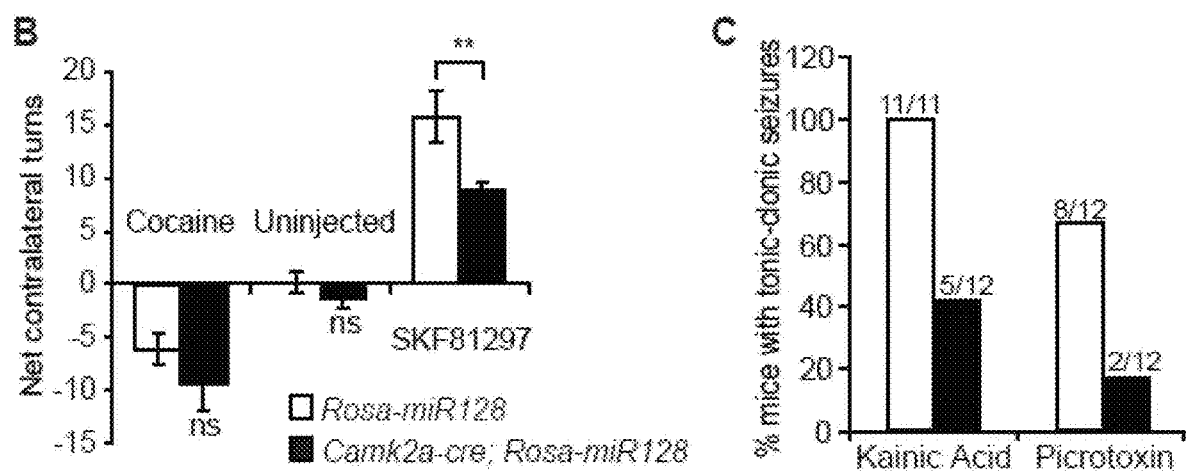
Figure 8A:
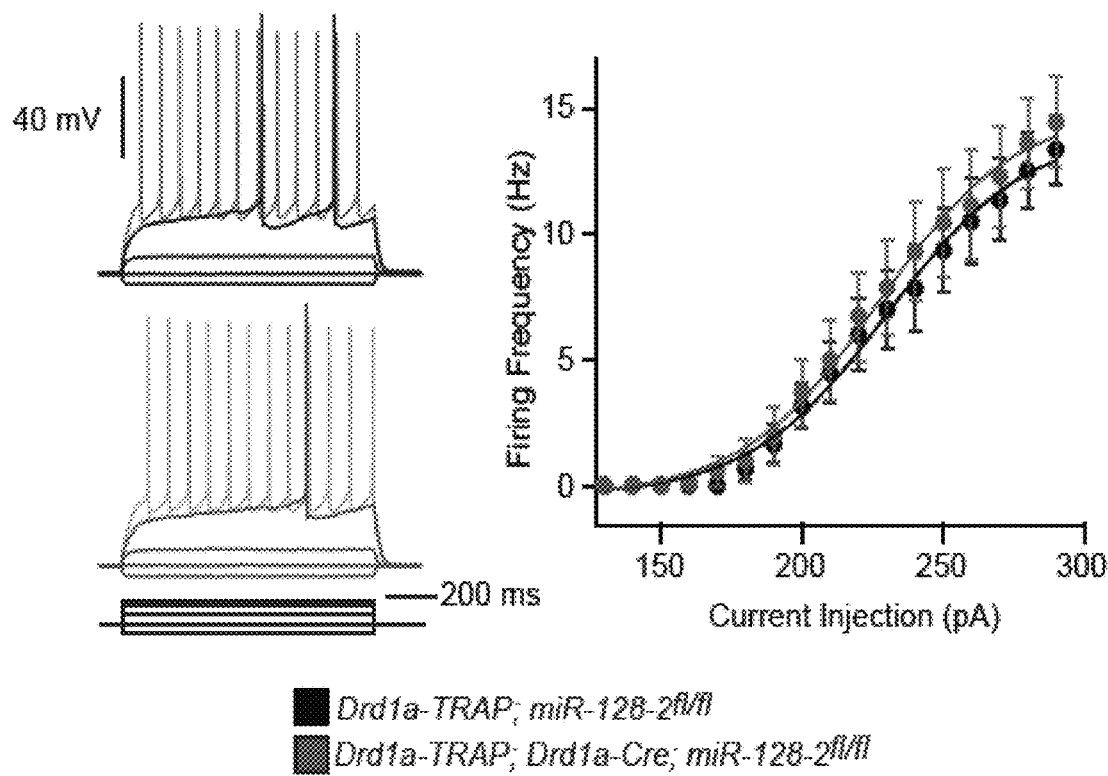
FIGS. 8A-8B show miR-128 deficient striatal D1-neurons display D1-neuron characteristic somatic excitability. (A, left) Representative D1-neuron prototypic responses of control (Drd1a-TRAP; miR-128-2fl/fl, top, black) and miR-128 deficient (Drd1a-TRAP, Drd1a-cre; miR-128fl/fl, bottom, red) D1-neurons to somatic current injections. D1-neurons were identified by eGFP-L10 expression, voltage traces are in response to −100, −50, +100, +190 and +250 pA. (A, right) Frequency-current (F-1) plot showing D1-neuron characteristic average firing frequencies to somatic current injection. No difference was observed between wild-type (black, n=6) and mutant (red, n=7) D1-neurons. Mann-Whitney nonparametric test, p>0.05. (B) miR-128 controls the number of functional spines in D1-neurons. 2 photon uncaging of glutamate on successive neighboring spine heads revealed similar success rates for producing somatic EPSCs in control and miR-128 deficient D1 neurons (n=5-6 cells, 40-48 spines per group, left), suggesting the increased spine density in (FIG. 3B) represents an increase in the number of spines with functional glutamate receptors. Glutamate uncaging-induced somatic EPSC amplitudes were similar in both groups (right).
Figure 8B:
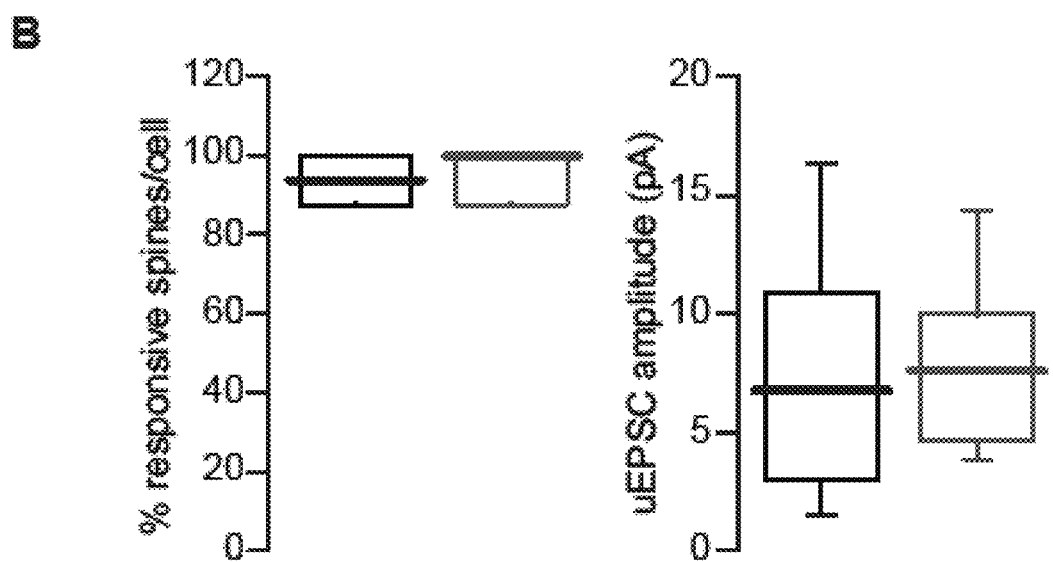
Figure 9A:
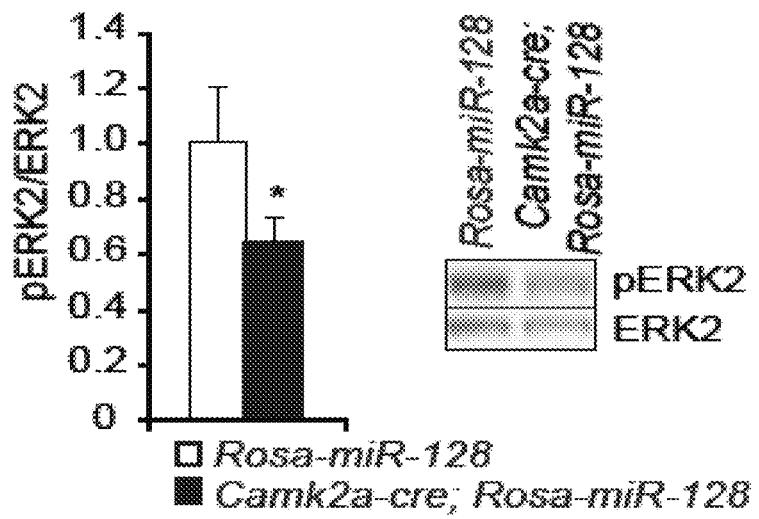
FIGS. 9A-9B show increased miR-128 expression in neurons suppresses ERK2 activation and protects against abnormal motor activity and seizures associated with chemically induced Parkinson's disease and seizures. (A) miR-128 overexpression in Camk2a-neurons suppresses ERK2 phosphorylation in mice. ERK2 phosphorylation levels in the striatum of transgenic Camk2a-cre; Rosa-miR-128 mutant and control mice (n=4 each) were quantified by Western blotting, normalized to total ERK2 expression, and displayed relative to mean control levels. Representative blot is shown. Welch's t-test, *p≤0.05. (B) miR-128 overexpression attenuates chemically triggered hyperresponsive motor behavior in mice. The scheme shows the standard rotational responses of wild type mice with unilateral 6-OHDA-induced lesion. 6-OHDA and vehicle were injected into the left and right striatum, respectively, and rotational responses to either cocaine (which inhibits endogenous dopamine reuptake at dopaminergic terminals and thereby increases synaptic dopamine levels) or the Drd1-agonist SKF81297 (specific activation of the dopamine D1 receptor (Drd1)) are assayed after a 3-week recovery period. Cocaine injections induce ipsilateral (towards the lesioned side) rotations due to the stronger activation of the unlesioned contralateral striatum that still contains the functional dopaminergic terminals. Injections of the Drd1-agonist SKF81297 induce contralateral rotations (away from the lesioned side) due to the abnormal hypersensitivity of D1-neurons to Drd1 activation after dopamine depletion in the lesioned, ipsilateral striatum.
Figure 9B:
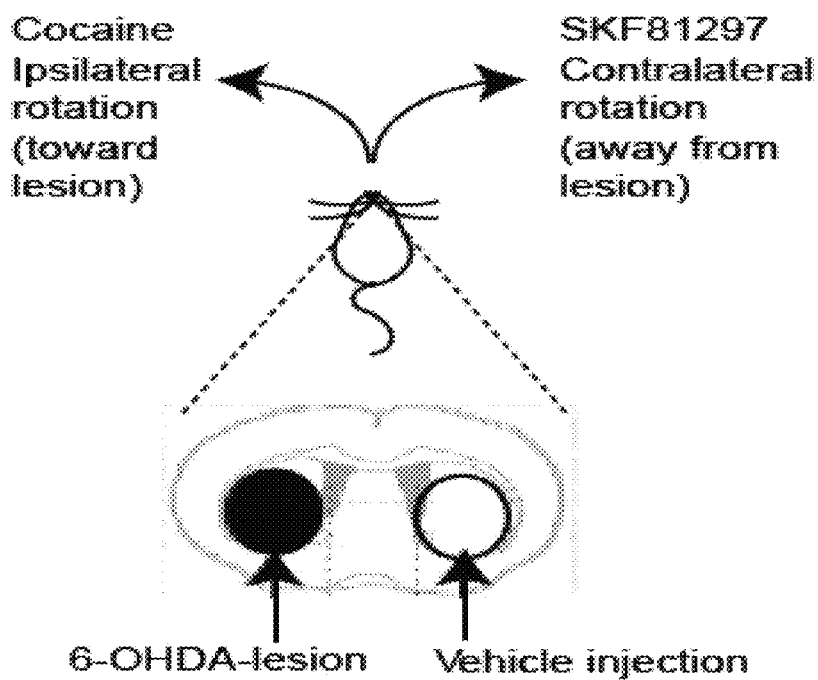
Figure 10:
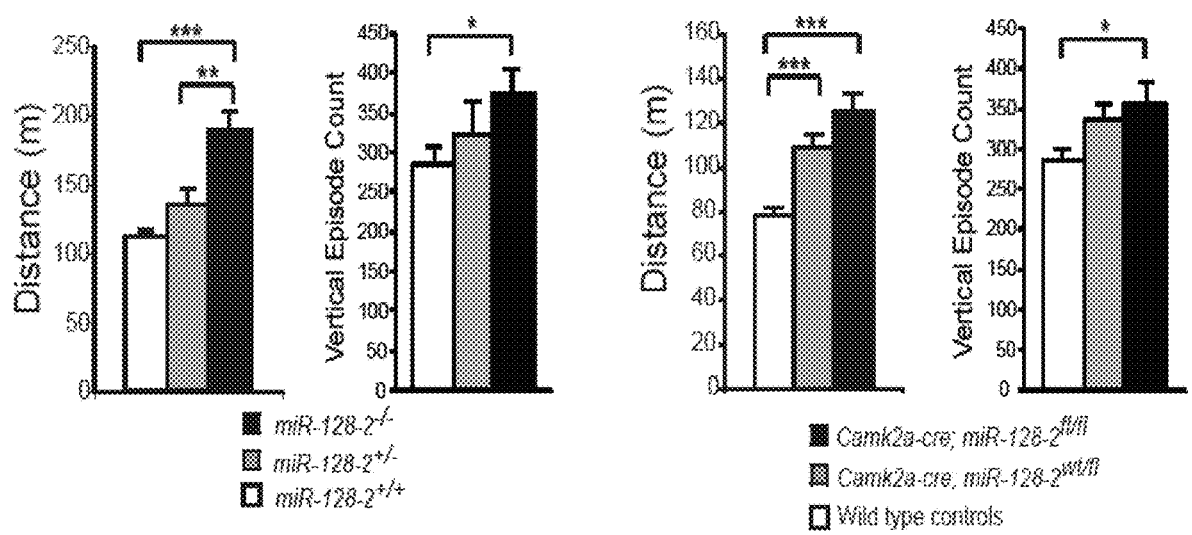
FIG. 10 shows that miR-128 depletion in postnatal neurons causes a dose-dependent increase in motor activity. miR-128 controls motor behavior in mice in a dose dependent fashion. Deficiency in miR-128-2 causes hyperactivity in mice. (Left panel) Motor activity in miR-128-2$^{−/−}$, miR-128-2$^{+/−}$, and wild-type littermate controls was determined by measuring total horizontal distance moved (in meters) and vertical rearing episode counts in a 60 min open field assay. Deficiency in miR-128-2 in postnatal neurons is responsible for the dose-dependent increase in motor activity. (Right panel) Motor activity in mice with a homozygous (Camk2a-Cre; miR-128$^{fl/fl}$), or heterozygous(Camk2a-Cre; miR-128$^{+/fl}$) depletion of miR-128-2, and their wild-type littermate controls was determined by measuring total horizontal distance moved (in meters) and vertical rearing episode counts in a 60 min open field assay.
Figure 11:
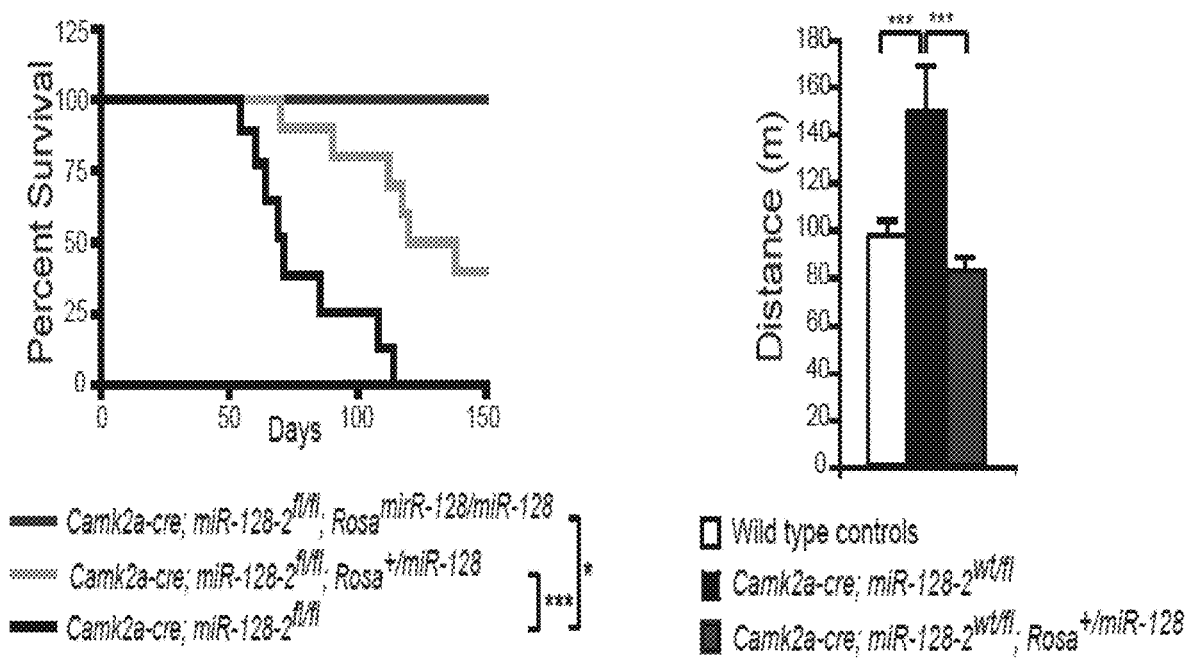
FIG. 11 shows a dose-dependent rescue of fatal epilepsy and hyperactivity by ectopically expressed miR-128. Ectopic expression of miR-128 normalizes hyper-locomotion and prevents death of Camk2a-cre; miR-128-2$^{fl/fl}$ mice in a dose-dependent fashion. (Left panel) The lifespans of Camk2a-cre; miR-128-2$^{fl/fl}$ mice in the absence (black) of presence of one (light blue) or two (dark blue) alleles of the ectopically expressed miR-128 are shown. (Right panel) Motor activity in Camk2a-cre; miR-128-2$^{fl/fl}$; Rosa-miR-128 (blue), Camk2a-cre; miR-128-2$^{fl/fl}$ (black), and wild-type mice (white) are shown.
Figure 12:
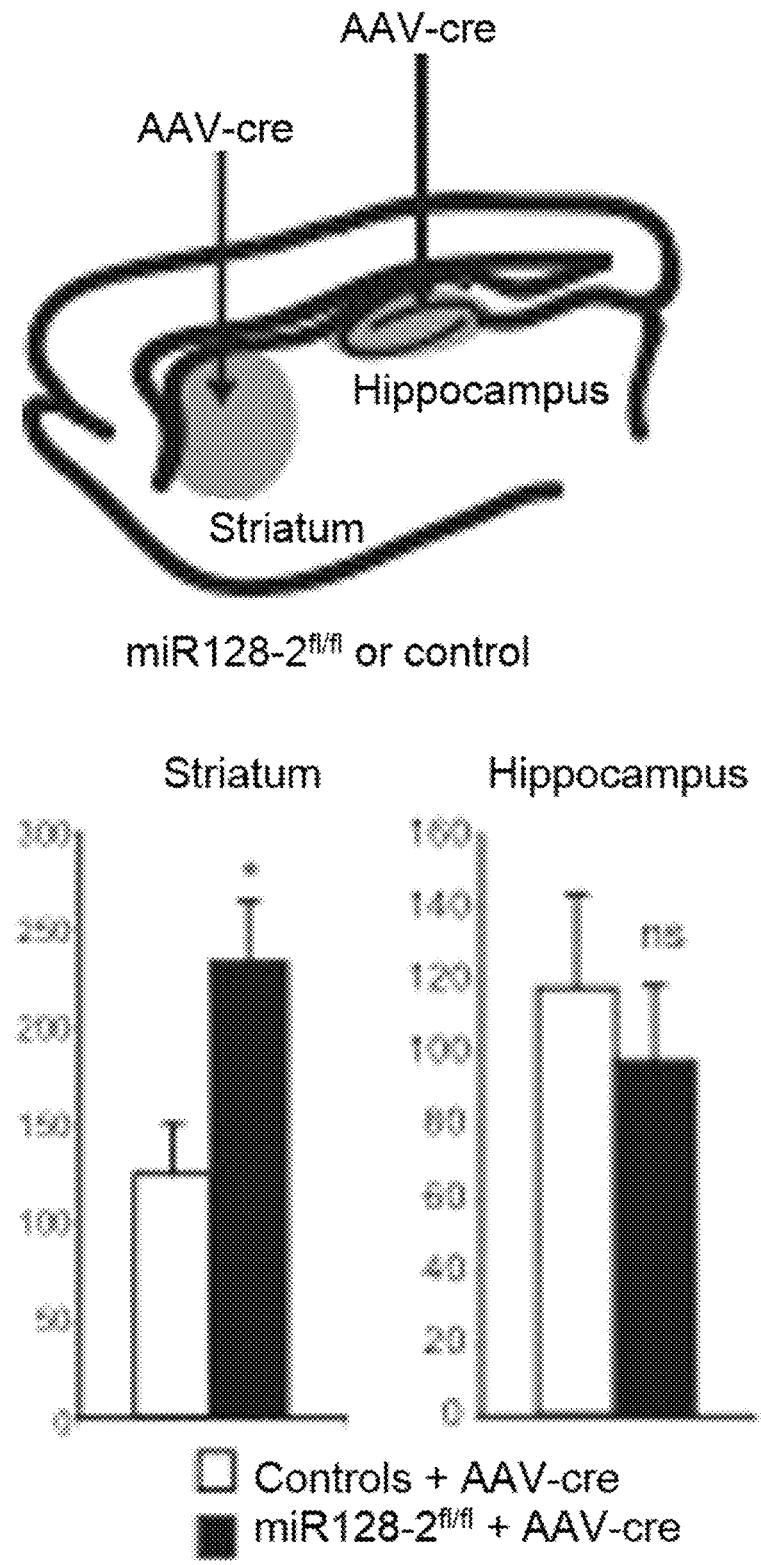
FIG. 12 shows virus-mediated deletion of miR-128 in the adult striatum but not the hippocampus leads to increase in motor activity similar to the genetic miR-128 depletion. AAV2-Cre mediated neuron-specific local depletion of miR-128 in adult mice in the striatum, but not the hippocampus, reproduces the increase in basal motor activity. AAV2-Cre was stereotactically injected into one of the two brain regions in 8-12 week old miR-128-2$^{fl/fl}$ mice and their respective wild-type littermates. Motor activity was determined by measuring total horizontal distance moved (in meters) in a 60 min open field assay. While most of the hippocampal injected mice died from severe seizures 1-2 month after virus injection, the majority of striatal-injected mice survived until sacrificed 6 month later.
Figure 13A:
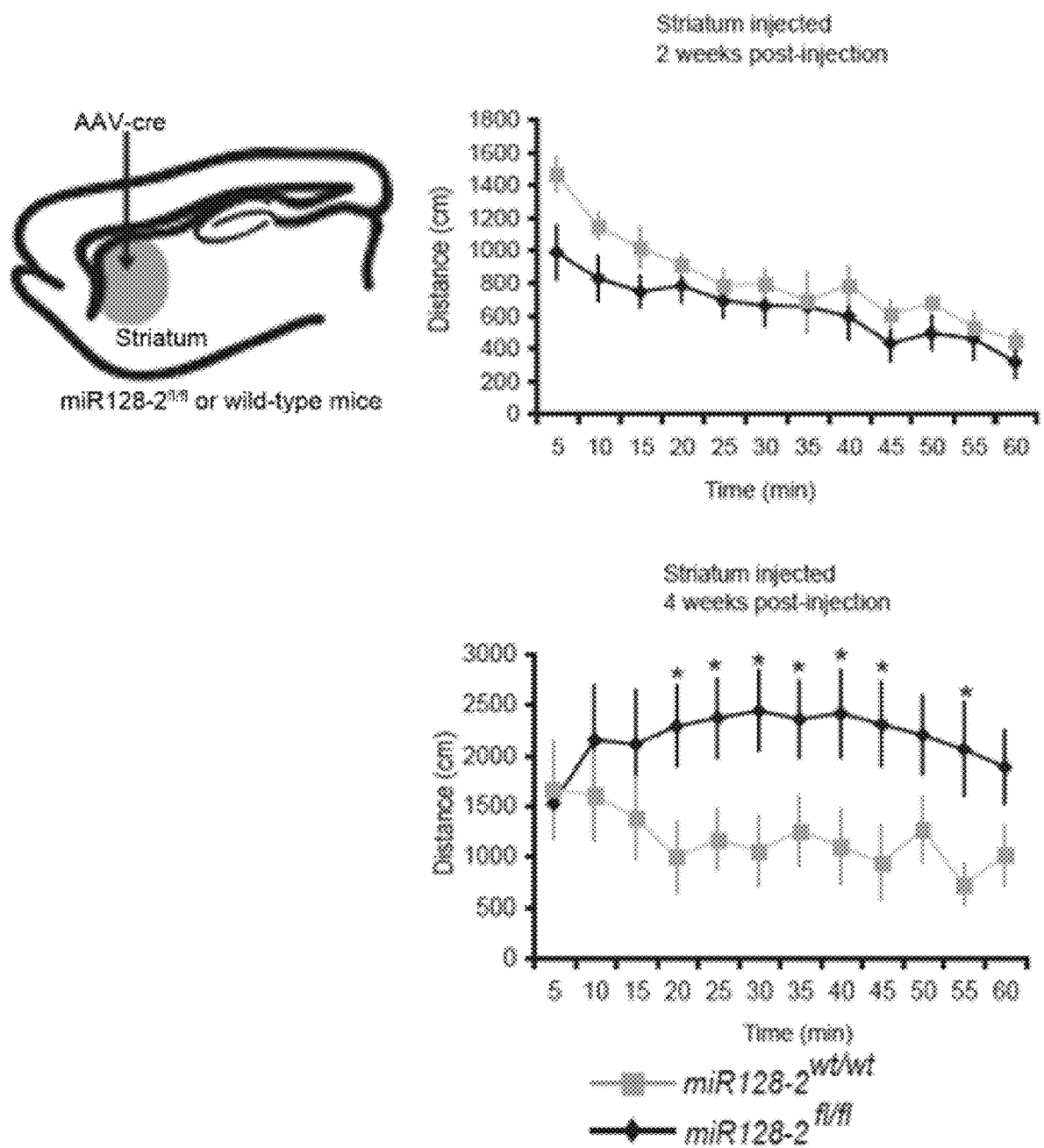
FIGS. 13A-13B show virus-mediated deletion of miR-128 in (A) the adult striatum but not in (B) the hippocampus leads to increase motor activity. AAV2-Cre mediated neuron-specific local depletion of miR-128 in adult mice in the striatum, but not the hippocampus, reproduces the increase in basal motor activity. AAV2-Cre was stereotactically injected into one of the two brain regions in 8-12 week old miR-128-2$^{fl/fl}$ mice and their respective wild-type littermates. Motor activity 2 weeks after surgery (prior to full virus expression) and 4 weeks after surgery (time of full virus expression) was determined by measuring total horizontal distance moved (in meters) in a 60 min open field assay. Data display clear effect of AAV-Cre virus induced increased in motor activity upon miR-128 depletion in the striatum but not the hippocampus. Collectively, AAV-Cre data indicate miR-128 expression in the striatum as regulator of basal activity and in the hippocampus as suppressor of spontaneous seizure activities.
Figure 13B:
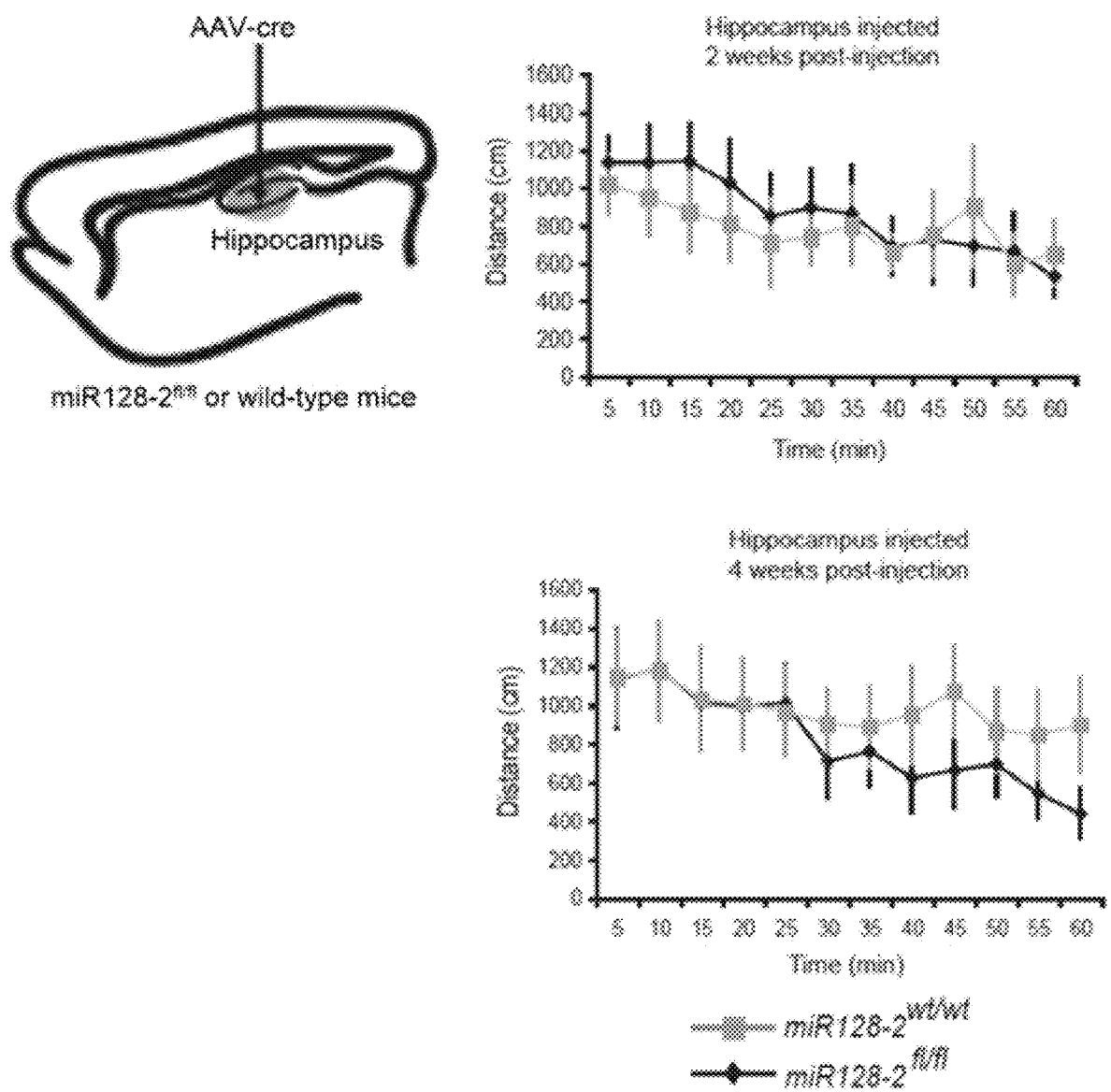
Figure 14:
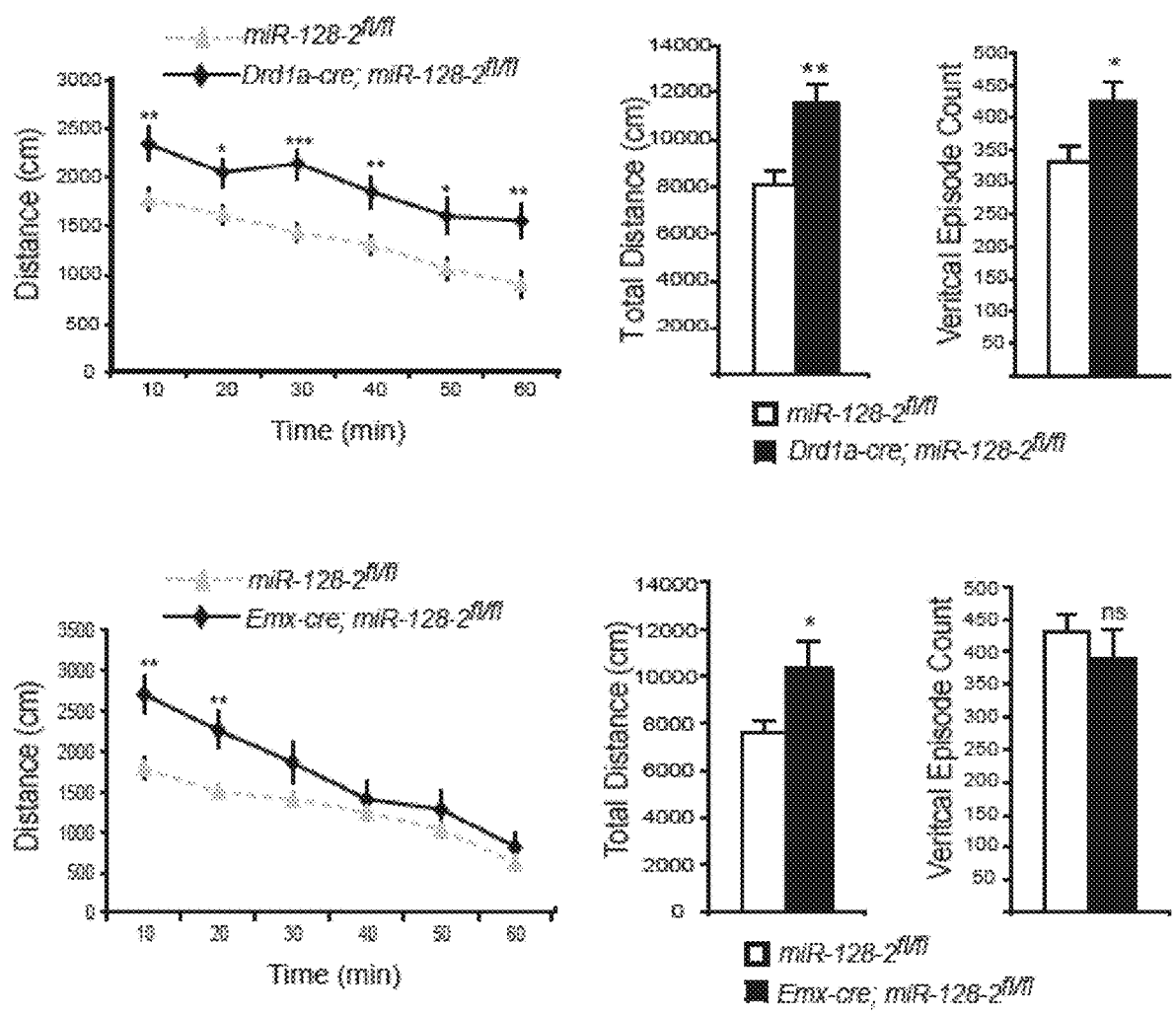
FIG. 14 shows contrary to the striatal D1-specific miR-128 depletion, cortex and hippocampus specific miR-128 depletion causes increases explorative activity only during first 20 min followed by normal basal activity in the open field. (Upper panel) Motor activity in Drd1a-cre; miR-128-2$^{fl/fl}$ mice or (lower panel) Emx-cre; miR-128-2$^{fl/fl}$ and their respective littermate controls were determined by measuring total horizontal distance moved (in meters) and vertical rearing episode counts in a 60 min open field assay.
Figure 15:
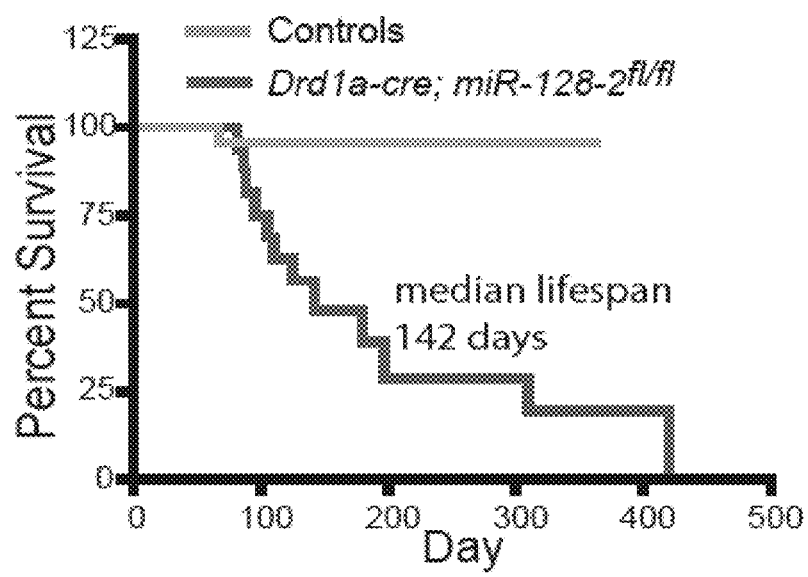
FIG. 15 shows cortex and hippocampus specific miR-128 depletion leads to premature seizure-induced death in mice with much earlier onset than upon striatal D1 neuron specific depletion. (Upper panel) The lifespans of Drd1a-cre; miR-128-2$^{fl/fl}$ mice and (lower panel) Emx-cre; miR-128-2$^{fl/fl}$ and their respective littermate controls are shown.
Figure 15:
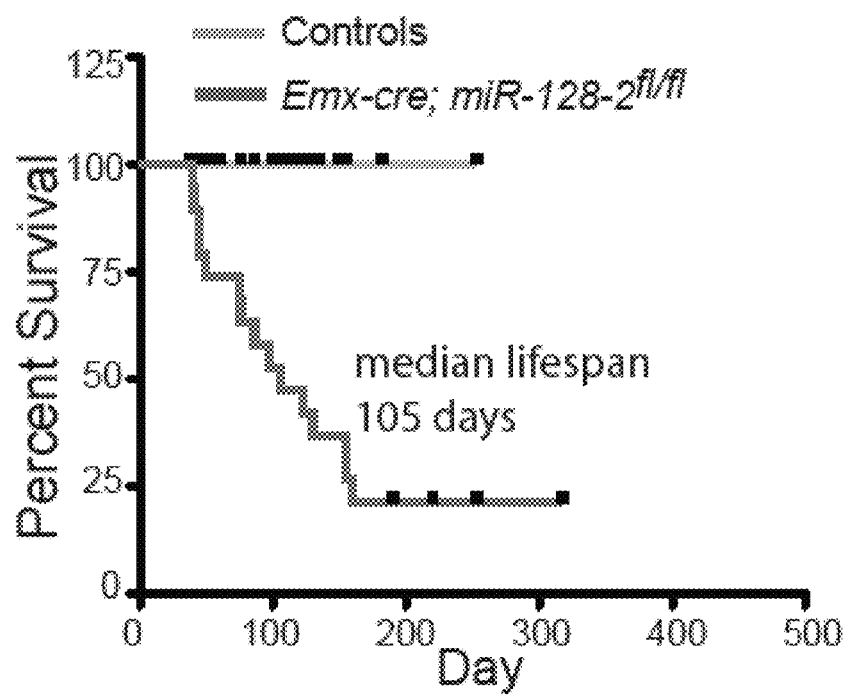
Figure 16:
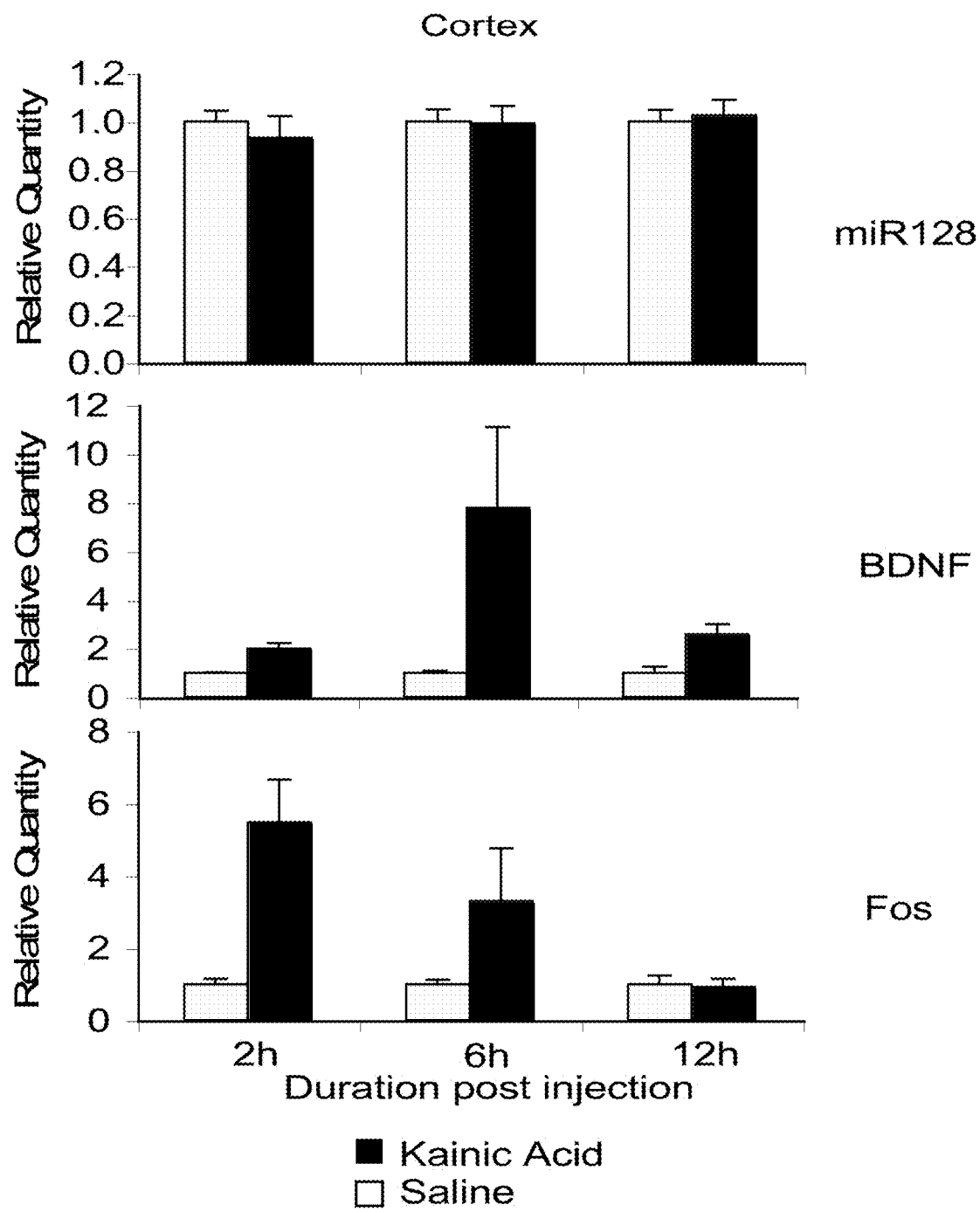
FIG. 16 shows opposite to the activity-induced genes BDNF and Fos, miR-128 expression remains stable and does not increase upon kainic acid induced seizures in the cortex of adult C57Bl6 wild type mice.
Figure 17:
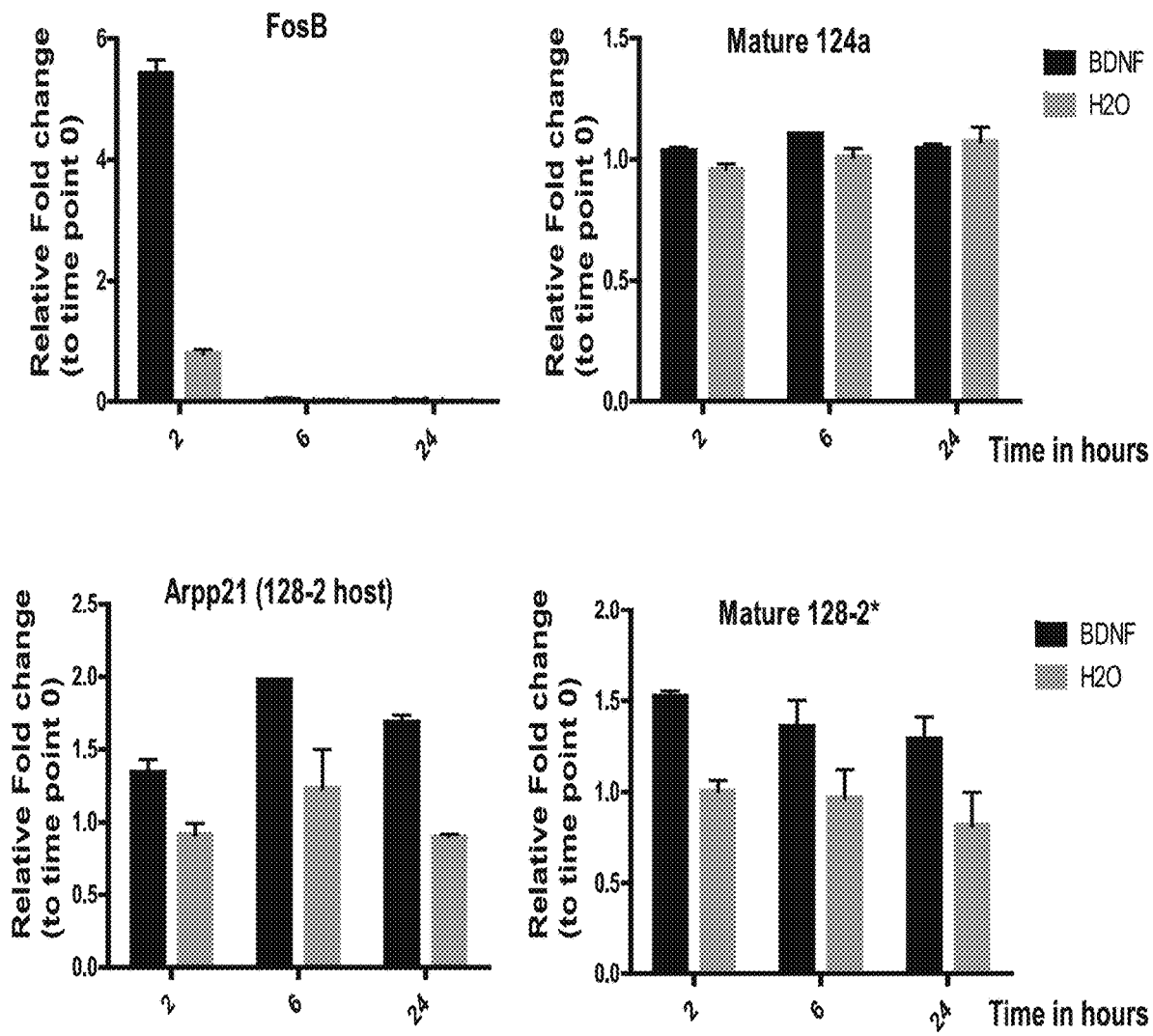
FIG. 17 shows BDNF induces Arpp21 and miR-128 in primary cultured striatal neurons. Primary striatal neuron cultures obtained from E18 mouse brain were treated on day 10 in vitro with 0.05 ng/ul brain-derived neurotrophic factor (BDNF) in water. RNA from cultures was prepared at 0, 2, 6 and 24 hours after stimulation and gene expression change were analyzed using the Taqman qRT-PCR assay. BDNF is a strong but transient inducer of the immediate early gene FosB (positive control shown upper left) but has no effect on the expression of the neuron-specific miRNA miR-124a (upper right). However, as the results show, BDNF treatment leads to a stable increase in miR-128 (lower right) and the miR-128 host gene Arpp21 (lower left). Data are shown as mean, error bars represent s.e.m., p-value was determined by 2-way ANOVA, FosB treatment 0.0014, time<0.0001. 124a treatment 0.1091, time 0.0861, Arpp21 treatment 0.0064, time 0.0190. miR-128-2 treatment 0.0160, time 0.2097.

Electrophysiological studies in striatal slices from Drd1a-cre; miR-128-2fl/fl mice revealed an increase in D1-neuron excitability. The miR-128 deficient D1-neurons showed normal membrane excitability at the soma (FIG. 8A), but displayed enhanced dendritic excitability (FIG. 3A) as well as a ~20% increase of functional dendritic spines (FIG. 3B, 8B). Furthermore, the ERK2 network in neuronal excitability and synaptic plasticity.

Enhanced ERK2 activation is linked to increased motor activity and seizures in mice. The hyper-activation of ERK2 and concomitant increase in D1-neuron sensitivity to dopamine occurs also during Parkinson-like disease in mice caused by chemically induced depletion of dopamine in the mouse striatum. The reduced levels of dopamine and concurrent increase of D1-neuron sensitivity result in hyper-responsiveness to the motor activity-inducing effects of dopamine. In humans, the D1-neuron hyper-responsiveness is one of the major causes of dyskinesia, a side effect of L-Dopa treatment in Parkinson's disease.

The inventors of the instant disclosure have discovered that miR-128 deficiency in striatal D1-neurons mimics the hypersensitivity of D1-neurons in mice suffering from Parkinson's-like syndrome. The inventors here show that the deficiency of miR-128 in D1-neurons enhances motor activity in response to Drd1-specific agonist treatment in mice (FIG. 3C). The D1-neuron hyper-responsiveness to the Drd1-agonist was also shown to be associated with an increase in ERK2 phosphorylation in the striatum of Drd1a-cre; miR-128-2fl/fl mice (FIG. 3D). The increase in dopamine sensitivity and enhanced ERK2 activation in mice with Parkinson's-like disease are accompanied by increased expression of dopamine-induced immediate early genes (IEG) in D1-neurons. Similarly, Drd1-agonist treatment enhanced IEG expression in miR-128 deficient D1-neurons as compared to the D1-neurons of control mice (FIG. 3E).

Figure 4C:
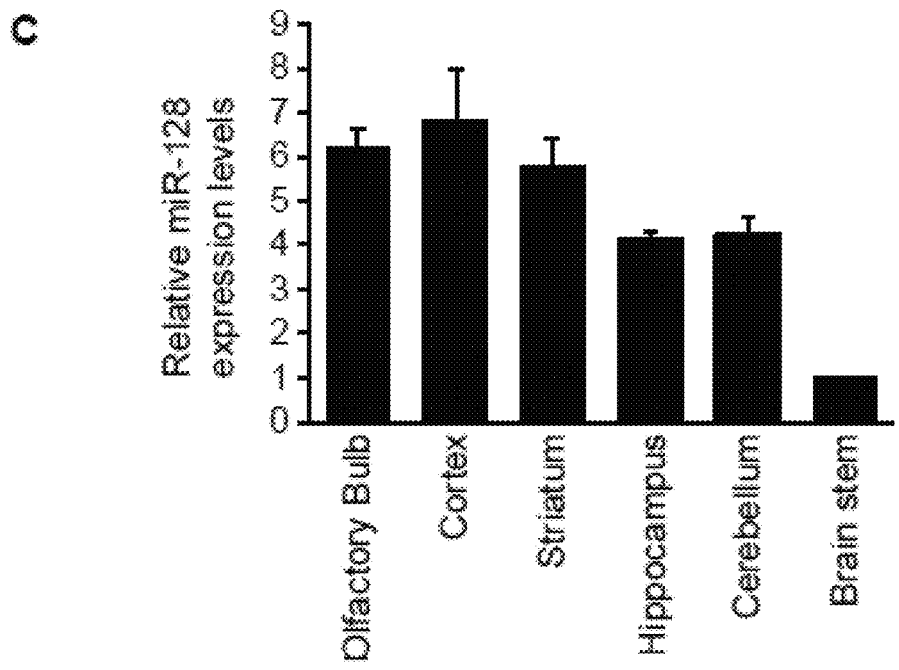

The increased locomotor activity characteristic of Drd1a-cre; miR128-2fl/fl mice was normalized by pharmacological inhibition of the mitogen-activated protein kinase kinase MEK1, a major activator of ERK2 in neurons. In vivo administered MEK1-specific inhibitor SL327 does not affect motor activity in wild type mice but does normalize ERK2 phosphorylation and motor activity in the mutant mice (FIG. 4A). In another finding, the inventors showed that the effect of increased miR-128 expression in adult neurons was to protect mice against abnormal motor activities associated with chemically-induced Parkinson's disease (FIG. 4B) and seizures (FIG. 4C).

In one aspect, the inventors of the instant application have discovered miR-128 as a modulator of signaling pathways that control neuronal excitability and motor activity. The human gene on chromosome 3p that encodes miR-128-2 has been linked to idiopathic generalized epilepsy. Changes in miR-128 or miR-128 target gene expression can be a potential cause of increased neuronal excitability and epilepsy in humans.

Accordingly, the present disclosure is directed to an agent capable of activating miR-128 for use in reducing the likelihood of spontaneous recurrent seizures in an individual or as an anti-epileptogenic agent in an individual having a brain injury likely to precipitate epilepsy, wherein the agent is delivered to the brain of the individual. The agent capable of activating miR-128 may be selected from the group consisting of chemically stabilized miR-128, a nucleic acid encoding miR-128, and a viral vector encoding miR-128.

In one aspect, the present disclosure is directed to a method for treating or reducing the likelihood for the development of seizures and/or epilepsy in a subject. This method may be achieved by administering miR-128 or an agent with 90 percent or more sequence homology to miR-128 to a brain injury site of the subject. miR-128 or the agent with 90 percent or more sequence homology to miR-128 may be administered intrathecally or intranasally, preferably such that the administration results in accumulation of the active agent in the hippocampus and/or the cortex. The miR-128 may be encoded by a vector. In particular, miR-128 may be encoded by a vector comprising a) promoter operatively linked to a nucleic acid molecule encoding miR-128; and b) a transcription termination sequence.

Unless defined otherwise, all technical and scientific terms used herein have the meaning commonly understood by one of ordinary skill in the art to which this invention belongs. Practitioners are particularly directed to Sambrook et al. (1989) Molecular Cloning: A Laboratory Manual, 2d ed., Cold Spring Harbor Press, Plainsview, N.Y. (1989), and Ausubel et al., Current Protocols in Molecular Biology (Supplement 47), John Wiley & Sons, New York (1999), for definitions and terms of the art.

The use of the word "a" or "an" when used in conjunction with the term comprising in the claims and/or the specification may mean "one," but it is also consistent with the meaning of "one or more," "at least one," and "one or more than one." The use of the term "or" in the claims is used to mean "and/or" unless explicitly indicated to refer to alternatives only, or the alternatives are mutually exclusive, although the disclosure supports a definition that refers to only alternatives and "and/or."

As used in this specification and claim(s), the words comprising (and any form of comprising, such as comprise and comprises), having (and any form of having, such as have and has), including (and any form of including, such as includes and include) or containing (and any form of containing, such as contains and contain) are inclusive or open-ended and do not exclude additional, unrecited elements or method steps.

As used herein, the terms approximately or about in reference to a number are generally taken to include numbers that fall within a range of 5% in either direction (greater than or less than) of the number unless otherwise stated or otherwise evident from the context. Where ranges are stated, the endpoints are included within the range unless otherwise stated or otherwise evident from the context.

In the context of the present invention, modulation and modulation of expression mean either an increase (stimulation) or a decrease (inhibition) in the amount or levels of a small non-coding RNA, nucleic acid target, an RNA or protein associated with a small non-coding RNA, or a downstream target of the small non-coding RNA (e.g., a mRNA representing a protein-coding nucleic acid that is regulated by a small non-coding RNA). In the context of the present invention, modulation of function means an alteration in the function of the small non-coding RNA or an alteration in the function of any cellular component with which the small non-coding RNA has an association or downstream effect.

The terms microRNA, miRNA, and MiR are interchangeable and refer to endogenous or artificial non-coding RNAs that are capable of regulating gene expression. It is believed that miRNAs function via RNA interference. Endogenous (e.g., naturally occurring) miRNAs are typically expressed from RNA polymerase II promoters and are generated from a larger transcript.

The terms polynucleotide, oligonucleotide, nucleic acid and nucleic acid molecule are used herein to include a polymeric form of nucleotides of any length, either ribonucleotides or deoxyribonucleotides. This term refers only to the primary structure of the molecule. Thus, the term includes triple-, double- and single-stranded DNA, as well as triple, double- and single-stranded RNA. It also includes modifications, such as by methylation and/or by capping, and unmodified forms of the polynucleotide. More particularly, the terms polynucleotide, oligonucleotide, nucleic acid and nucleic acid molecule include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms polynucleotide, oligonucleotide, nucleic acid and nucleic acid molecule, and these terms will be used interchangeably.

Homologous polynucleotides typically have at least 70% homology, preferably at least 80%, 90%, 95%, 97% or 99% homology with the relevant sequence, for example over a region of at least 5, 10, 20, 40 more contiguous nucleotides (of the homologous sequence). Homology may be calculated based on any method in the art. For example, the UWGCG Package provides the BESTFIT program which can be used to calculate homology. The PILEUP and BLAST algorithms can be used to calculate homology or line up sequences (typically on their default settings). Software for performing BLAST analyses is publicly available through the National Center for Biotechnology Information (URL: www.ncbi.nlm.nih.gov).

Administering a nucleic acid, such as a microRNA, siRNA, piRNA, snRNA, antisense nucleic acid, or lncRNA to a cell comprises transducing, transfecting, electroporating, translocating, fusing, phagocytosing, shooting or ballistic methods, etc., i.e., any means by which a nucleic acid can be transported across a cell membrane.

As far as routes of administration of therapeutic agents of the present invention are concerned, in one example, the blood-brain barrier is a concern. That is, an obstacle for the development of RNA-based therapeutic approaches for brain pathologies is the blood-brain barrier (BBB). The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000- fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain.

The present invention also provides pharmaceutical compositions. Such compositions comprise a therapeutically effective amount of the therapeutic, and a pharmaceutically acceptable carrier. In a specific embodiment, the term pharmaceutically acceptable means approved by a regulatory agency of the Federal or a state government or listed in the U.S. Pharmacopeia or other generally recognized pharmacopeia for use in animals, and more particularly in humans. In this specification, the term therapeutically effective amount should be taken to mean an amount of therapeutic which results in a clinically significant inhibition, amelioration or reversal of development or occurrence of seizures.

The term carrier refers to a diluent, adjuvant, excipient, or vehicle with which the therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration. Generally, the ingredients are supplied either separately or mixed together in unit dosage form, for example, as a dry lyophilized powder or water free concentrate in a hermetically sealed container such as an ampoule or sachette indicating the quantity of active agent.

In the context of the present disclosure, in certain embodiments, the therapeutic agent is administered intranasally or intrathecally. The goal of the mode of administration is to enable the therapeutic agent to reach its target sight, the central nervous system. In one embodiment, the target location for the therapeutic agents of the present disclosure is the cortex and/or the hippocampus.

Delivery of biologics across the blood brain barrier and into the central nervous system is better achieved by certain means of administration and/or drug formulation as would be understood to one of ordinary skilled drug delivery Pharmacologist. The compositions of the present disclosure may further include agents which improve the mucoadhesivity, nasal tolerance, or the flow properties of the composition, mucoadhesives, absorption enhancers, odorants, humectants, and preservatives. Suitable agents which increase the flow properties of the composition when in an aqueous carrier include, for example, sodium carboxymethyl cellulose, hyaluronic acid, gelatin, algin, carageenans, carbomers, galactomannans, polyethylene glycols, polyvinyl alcohol, polyvinylpyrrolidone, sodium carboxymethyl dextran and xantham gum. Suitable absorption enhancers include bile salts, phospholipids, sodium glycyrrhetinate, sodium caprate, ammonium tartrate, gamma. aminolevulinic acid, oxalic acid, malonic acid, succinc acid, maleic acid and oxaloacetic acid. Suitable humectants for aqueous compositions include, for example, glycerin, polysaccharides and polyethylene glycols. Suitable mucoadhesives include, for example, polyvinyl pyrrolidone polymer.

Another aspect of the invention is pharmaceutical compositions that may further include permeation enhancer agents that enhance delivery of the agent to the central nervous system via intranasal administration. Furthermore, absorption enhancers facilitate the transport of molecules through the mucosa, which includes the mucous, and the epithelial cell membrane. A variety of absorption enhancer classes have been described, including mucoadhesives, ciliary beat inhibitors, mucous fluidizers, membrane fluidizers, and tight junction modulators.

The term transfection is used to refer to the uptake of foreign DNA or RNA by a cell. A cell has been transfected when exogenous DNA or RNA has been introduced inside the cell membrane. A number of transfection techniques are generally known in the art. See, e.g., Sambrook et al. (2001) Molecular Cloning, a laboratory manual, 3rd edition, Cold Spring Harbor Laboratories, New York. Such techniques can be used to introduce one or more exogenous DNA or RNA moieties into suitable host cells. The term refers to both stable and transient uptake of the genetic material, and includes uptake, for example, of microRNA, siRNA, piRNA, lncRNA, or antisense nucleic acids. The term transformation refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

Recombinant host cells, host cells, cells, cell lines, cell cultures, and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

Pharmaceutically acceptable excipient or carrier refers to an excipient that may optionally be included in the compositions of the invention and that causes no significant adverse toxicological effects to the patient. Pharmaceutically acceptable salt includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

The terms subject, individual, and patient, are used interchangeably herein and refer to any mammalian subject for whom diagnosis, prognosis, treatment, or therapy is desired, particularly humans. Other subjects may include cattle, dogs, cats, horses, and so on.

The encoding sequence of the invention (e.g., the miRNA precursor encoding sequence or longer carrier encoding sequence) can be present in the construct in operable linkage with a promoter. Appropriate promoters can be selected based on the host cell and effect sought. Suitable promoters include constitutive and inducible promoters, such as inducible RNA polymerase II (polII)-based promoters. The promoters can be tissue specific, such promoters being well known in the art. Examples of suitable promoters include the tetracycline inducible or repressible promoter, RNA polymerase I or III-based promoters, the pol II dependent viral promoters such as the CMV-IE promoter, and the polIII U6 and H1 promoters. The bacteriophage T7 promoter can also be used (in which case, it will be appreciated, the T7 polymerase must also be present).

The constructs of the invention can be introduced into host cells using any of a variety of approaches. Infection with a viral vector comprising the construct can be effected. Examples of suitable viral vectors include replication defective retroviral vectors, adenoviral vectors, adeno-associated vectors and lentiviral vectors. Transfection with a plasmid comprising the construct is an alternative mode of introduction. The plasmid can be present as naked DNA or can be present in association with, for example, a liposome. The nature of the delivery vehicle can vary with the host cell.

In vivo delivery of the construct (e.g., present in a viral vector) can be carried out using any one of a variety of techniques, depending on the target tissue. Delivery can be, as appropriate, by direct injection, inhalation, intravenous injection or other physical method (including via microprojectiles to target visible and accessible regions of tissue (e.g., with naked DNA)). Administration can be by syringe needle, trocar, cannula, catheter, etc., as appropriate.

Cultured cells suitable as hosts in accordance with the invention include both primary cells and cell lines. The cells can be human cells, including human stem cells. A construct of the invention encoding an miRNA can be introduced into cultured cells to inactivate a specific gene of unknown function. Silencing the gene using the method of the invention can be used as an approach to assess its function. Alternatively, a construct encoding an miRNA can be introduced into cells to be implanted into a human or non-human animal for therapeutic purposes.

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), is hereby expressly incorporated herein by reference.

EXAMPLES

The invention, having been generally described, may be more readily understood by reference to the following examples, which are included merely for purposes of illustration of certain aspects and embodiments of the present invention, and are not intended to limit the invention in any way.

Materials and Methods

Animals

Mice were housed at two to five animals per cage with a 12-hour light/dark cycle (lights on from 0700 to 1900 hours) at constant temperature (23° C.) with ad libitum access to food and water. All animal protocols were approved by IACUC at The Rockefeller University, The Northwestern University, and Icahn School of Medicine at Mount Sinai.

Generation of Mice

Generation of Mice with a Conditional Deletion of miR-128-1 and miR-128-2:

Subcloning of targeting vectors: A region of the miR-128-1 or miR-128-2 genomic locus containing the arms of homology was recombinogenically subcloned from a BAC clone (miR128-1: RP24-574G14, miR128-2: RP24-242F13, C57Bl6J, CHORI, Oakland CA, USA) into pBlueScriptIIKS+ using amplicons that insert an AscI site and a XhoI site to flank the subcloned region.

PCR primers used for subcloning:

mir-128-1

```
mir-128-1
                                            (SEQ ID NO: 2)
5'ccttcatgttatgcctcatcctttatcacacaaatctgtgtagtt
ttcggcgcgccattcgccctatagtgagtcg
                                            (SEQ ID NO: 3)
5'
aatcttctaaatttccatttgagcacctagttcatatgtaatttagatt
cctcgaggcttggcgtaatcatggtc mir-128-2
                                            (SEQ ID NO: 4)
5'cgaaaatattttcatttattcttcgaaactttcatacattcataca
atgtggcgcgccattcgccctatagtgagtcg
                                            (SEQ ID NO: 5)
5'tcaggcctgccagccttctgtctactgtttaatgactgacagccagt
gaactcgaggcttggcgtaatcatggtc
```

Modification of Targeting Vector for miR-128-1:

pZeroloxP-FRT-neoR-FRT(−) was modified to replace the unique EcoRI site with a unique SmaI site. The following oligonucleotide fragments were annealed and inserted into the EcoRI site:

```
                                            (SEQ ID NO: 6)
    5' aattgcatcgcatgggtcacgacgagatcccgggc (SEQ ID NO: 7)
    5' aattgcccgggatctcgtcgtgacccatgcgatgc
```

The modified plasmid was digested with NsiI, and the fragment containing a single loxP site and the FRT-flanked neo gene was inserted into the unique NsiI site in the targeting vector and screened for proper orientation. For insertion of the second loxP site, the following oligonucleotide fragments were annealed and inserted into the unique SpeI site:

```
                                            (SEQ ID NO: 8)
5' ctagaataacttcgtatagcatacattatacgaagttatgaattct (SEQ ID NO: 9)
5' ctagagaattcataacttcgtataatgtatgctatacgaagttatt
```

Modification of Targeting Vector for miR-128-2 pZeroloxP-FRT-neoR-FRT(−) was modified by digesting the plasmid with SacI and ApaI and annealing and inserting the following oligonucleotide fragments:

```
                                            (SEQ ID NO: 10)
5'ggaagttcctatactttctagagaataggaacttcggaataggaact
tcagagctcatcgagcccgggtagacggccc (SEQ ID NO: 11)
5'gtctacccgggctcgatgagctctgaagttcctattccgaagttcct
attctctagaaagtataggaacttccagct
```

The plasmid was further digested with Acc65I and the following oligonucleotides were annealed and inserted:

```
                                            (SEQ ID NO: 12)
5' gtaccccgggataacttcgtatagcatacattatacgaagttata
agcttc (SEQ ID NO: 13)
5' gtacgaagcttataacttcgtataatgtatgctatacgaagttatc
ccgggg
```

The modified plasmid was digested with SmaI and the fragment containing a single loxP site and the FRT-flanked neo gene was inserted into the unique SmaI site in the targeting vector and screened for proper orientation. For insertion of the second loxP site, the following oligonucleotides were annealed and inserted into the unique HindIII site:

```
                                            (SEQ ID NO: 14)
5' agctaataacttcgtatagcatacattatacgaagttatggatcct (SEQ ID NO: 15)
5' agctaggatccataacttcgtataatgtatgctatacgaagttatt
```

For both targeting vectors, the modified regions of homology were excised from pBluescript with XhoI and AscI digests and inserted into similarly digested pDTA-TK to produce the final targeting constructs. The targeting constructs were linearized with NotI, and E14 CY2.4 embryonic stem cells (homozygous C57Black/6JTyr-C-2J background with natural mutation in tyrosinase gene) were transfected and screened for successful recombination using a Southern probe. Positive clones were confirmed using an alternate Southern probe and by PCR sequencing of the modified region. Positive clones were used to produce chimeric mice as described. Chimeras were crossed to C57BL6/J mice, and germline transmission was assessed by coat color, PCR and Southern blot analysis. Germline deletion of the FRT-flanked neo gene was accomplished by crossing mice carrying the targeted alleles with FLPe-transgenic mice (Jackson Laboratory). Germline deletion of miR-128-1 and miR-128-2 to generate miR-128-1−/− and miR-128-2−/− mice was achieved by crossing mice carrying floxed alleles to transgenic mice that express Cre-recombinase driven by the ubiquitously expressed CMV promoter (CMV-cre mice, Jackson Laboratory).

Postnatal, neuron-specific deletion in the mouse forebrain was achieved by breeding mice carrying floxed alleles (miR-128-2fl/fl) to Camk2a-cre mice (31) to generate Camk2a-cre; miR-128-2fl/fl mice. Drd1a-cre (EY262) and A2a-cre (KG139) transgenic mice were obtained from Gensat (32) and crossed with miR-128-2fl/fl to generate Drd1a-cre; miR-128-2fl/fl and A2a-cre; miR-128-2fl/fl mice.

Routine genotyping of miR-128-1 mice was performed using following primers:

```
                                            (SEQ ID NO: 16)
        5'-tctggaccaaatgaaccaaag (SEQ ID NO: 17)
        5'-ccgcaatgctgcctatattc (SEQ ID NO: 18)
        5'-gcctgaagaacgagatcagc (SEQ ID NO: 19)
        5'-gcagtcatgcaagcagctat
```

Wild type allele: 194 bp
Null allele: 282 bp
Floxed allele: 336 bp

Routine genotyping of miR-128-2 mice was performed using following primers:

```
                                            (SEQ ID NO: 20)
        5'-cgcctttagtttcccacag (SEQ ID NO: 21)
        5'-gaccacacagcaagcaggta (SEQ ID NO: 22)
        5'-aaagacgggaccattcacat (SEQ ID NO: 23)
        5'-tctctcgtgggatcattgttt
```

Wild type allele: 185 bp
Null allele: 531 bp
Floxed allele: 306 bp

Generation of Mice with a Neuron-Specific Overexpression of miR-128-2.

The targeting vector for homologous recombination at the ROSA26 locus was generously provided by K. Rajewsky (30). A 1 kb region including miR-128-2 hairpin was amplified from genomic DNA with the following primers and cloned into the unique XhoI site in the targeting vector:

```
                                            (SEQ ID NO: 24)
    5' aaaggcgcgccacgtgACTAAAAGGCGCGAGGAGAT (SEQ ID NO: 25)
    5' aaaggcgcgccTACGCATTCCTGTACGGTTG
```

Modified targeting vector was linearized by NotI and used to generate chimeras as above. Successful germline transmission was assessed by coat color and confirmed by PCR and Southern analysis. Routine genotyping of Rosa-miR-128 mice was performed using the following primers:

```
                                            (SEQ ID NO: 26)
        5'-gagttctctgctgcctcctg (SEQ ID NO: 27)
        5'-ggaaagtccctattggcgtta (SEQ ID NO: 28)
        5'-tgctgcataaaaccccagat
```

Wild type allele: 292 bp
Rosa-miR-128 targeted allele: 408 bp

Postnatal, neuron-specific miR-128-2 overexpression in the mouse forebrain was achieved by breeding homozygous Rosa-miR-128 mice to Camk2a-cre mice (31) to generate Camk2a-cre; Rosa-miR-128 mice. Rosa-miR-128 mice were bred to Camk2a-cre; miR-128-2fl/fl mice to generate Camk2a-cre; miR-128-2fl/fl; Rosa-miR-128 rescue mice.

Generation of Mice with Neuron-Specific FLAG Tagged-Ago2 Expression:

Transgenic mice expressing a Cre-inducible FLAG-HA2-tagged Ago2 under the control of the ROSA26 promoter were generated as previously described (9, 30). The STOP-eGFP-ROSA26TV vector was a gift from K. Rajewsky, Harvard Medical School, Boston, MA. Rosa-Stopfl/fl-Flag-Ago2 mice were bred to Camk2a-cre transgenic mice (kindly provided by G. Schuetz, German Cancer Research Center, Heidelberg, Germany (31)) to generate Camk2a-cre; Rosa-Stopfl/fl-Flag-Ago2 mice.

RNA Preparation

Mice were anesthetized with C02, and the respective brain regions or peripheral organs were rapidly dissected and frozen in liquid nitrogen until further processing. RNA extraction from frozen samples was performed using the TRIzol/Chloroform technique according to manufacturer's instructions (Invitrogen Corporation, Carlsbad, CA). After extraction, RNA was precipitated overnight at −80 C in isopropanol with 0.15M sodium acetate, washed twice with 70% ethanol, air-dried, and resuspended in RNase-free water.

D1-Neuron Specific TRAP Analysis

Mice with D1-neuron specific loss of miR-128-2 (Drd1a-cre; miR-128-2fl/fl) were crossed to mice carrying D1-MSN specific expression of eGFP-tagged ribosome protein L10 ((11), D1-TRAP). Polyribosome-associated mRNAs from 6 week old, age- and sex-matched Drd1a-cre; Drd1a-TRAP; miR-128fl/fl and Drd1a-TRAP; miR-128fl/fl mice (n=5/genotype) were obtained as previously described (11). eGFP-labeled ribosomes and associated mRNAs were immunoprecipitated using a mix of two monoclonal anti-GFP antibodies (50 μg of clones #19C8 and #19F7 for each IP, available at Sloan-Kettering Monoclonal Antibody Facility). Purified mRNA was amplified and processed for microarray and qPCR analysis using the Affymetrix two-cycle cDNA Synthesis kit (Affymetrix, Santa Clara, CA) as previously described (11). Affymetrix Mouse Genome 430 2.0 arrays were used in all experiments. Information regarding the array design and features can be found at www.affymetrix.com. Mouse Genome 430 2.0 arrays were scanned using the GeneChip Scanner 3000 (Affymetrix, Santa Clara, CA) and globally scaled to 150 using the Affymetrix GeneChip Operating Software (GCOS v1.4). GeneChip files (.cel) were imported into GeneSpring software (Agilent Technologies, Santa Clara, CA) and processed with RMA algorithm, and expression values on each chip were normalized to median of all samples. D1-neuron specific ribosome-associated mRNAs from two independent experiments were analyzed. All probes with differential expression and p-value≤0.05 using 2-way ANOVA (genotype) were considered significantly changed in the absence of miR-128-2.

Dataset from TRAP experiments were analyzed by SYLAMER algorithm to determine if miR-128 targets were more abundant among genes upregulated in the absence of miR-128 compared to genes downregulated in the absence of miR-128. Genes on the array were ranked from most upregulated to most downregulated genes in Drd1a-cre; Drd1a-TRAP; miR-128fl/fl as compared to Drd1a-TRAP; miR-128fl/fl mice according to fold-change t-statistic. The enrichment analysis was obtained by SYLAMER with Bonferroni-corrected p-value threshold of 0.05 (http://www.ebi.ac.uk/enright-srv/sylarray/).

TaqMan Quantitative RT-PCR for mIRNA and mRNA Analysis

Relative expression levels of mature miRNAs and mRNAs were measured by TaqMan assays using total extracted RNA from brain samples, according to manufacturer's protocol (Life Technologies, Carlsbad, CA). Purified RNA samples were assayed by qRT-PCR for relative gene expression using pre-designed TaqMan gene expression assays from Applied Biosystems (ABI) as recommended by the manufacture. The following pre-designed TaqMan gene expression assays from Applied Biosystems (ABI) were used: miR-128 (Assay ID 002216), sno135 (Assay ID 001230), miR-124a (Assay ID 001182), Fosb Mm00500401_m1, Fosl2 Mm00484442_m1, Arc Mm00479619_g1, JunB Mm04243546_s1, Darpp-32 Mm00454892_m1, Btg2 Mm00476162_m1, Gadd45g Mm01352550_g1, Dusp1 Mm00457274_g1, Nr4a1 Mm01300401_m1, Jun Mm00495062_s1, Actb Mm00607939_s1, Arpp-21 Mm00473630_m1 (exon spanning probe detects exons that are common to all Arpp-21 isoforms), Arpp21 Mm00473645_m1 (exon spanning probe that specifically detects the long TARPP-isoform of Arpp-21). Cycle counts for miRNA quantification were normalized to snoRNA135 or miR-124a as indicated, and cycle counts for mRNA quantification were normalized to Actb or Gapdh. Relative expression ($\Delta$Ct) and quantification (RQ=2-$\Delta\Delta$C) for each mRNA were calculated using RQ Manager Software and the $\Delta\Delta$Ct method as suggested. Calculation of standard deviation (SD$\Delta$Ct=(SDtarget2+SDref2)1/2) and error bars (RQ1=2^(−($\Delta\Delta$Ct+SD$\Delta\Delta$Ct)), and RQ2=2^(−($\Delta\Delta$Ct-SD$\Delta\Delta$Ct))) was performed according to ABI technical literature Part Number 4371095 Rev B.

Pathway Analysis

Bioinformatic network and pathway analyses of the 154 miR-128 target genes was performed using IPA (Ingenuity Systems, Redwood City, CA) and the Database for Annotation, Visualization and Integrated Discovery (DAVID) version 6.7 (david.abcc.ncifcrf.gov/).

Protein Preparation and Expression Analysis

Mice were anesthetized with C02 and the cortex, hippocampus, and striatum were rapidly dissected and frozen in liquid nitrogen until further processing. Samples were sonicated on ice in 1% SDS solution supplemented with protease inhibitor (Roche, Switzerland) and phosphatase inhibitor, and boiled for 10 minutes. Protein concentration was determined using BCA protein assay kit (ThermoFisherScientific, USA) according to the manufacturer's instructions. Protein samples were diluted in equal volume of 2×LDS sample buffer (Invitrogen) and supplemented with DTT to a final concentration of 200 mM (Sigma). 25 ug of protein samples were separated on 4-12% Bis-tris precast denaturing gels (Invitrogen), transferred onto PVDF membranes, and blocked with 5% milk in TBS-0.1% Tween (TBST) solution for 1 hour at room temperature. Membranes were probed with primary antibodies diluted in 5% milk-TBST solution overnight at 4 C. Membranes were then washed and probed with horseradish-peroxidase conjugated anti-mouse (GE) or anti-rabbit IgG secondary antibody (GE) for 1 hour at room temperature. Membranes were developed using enhanced chemiluminescence substrate (PerkinElmer, USA) and exposed on BioMax film (Kodak, USA). Exposed films were scanned, and protein bands were quantified using ImageJ Software (NIH, USA). Protein quantities were normalized using beta-Actin, phosphoprotein levels were normalized to total non-phosphorylated protein levels, and all values plotted relative to control littermate sample. The following primary antibodies were used: total ERK1/2 (137F5), phosphoERK1/2 (Thr202/Tyr204), Arpp21 (mouse monoclonal 6A, gift. A. Nairn), beta-Actin (Abcam), PEA15a (H80) (Santa Cruz), D4ertd22e (Atlas).

ELISA Assay

The ELISA quantification was performed using the PathScan MAP kinase Multi-Target Sandwich ELISA kit (Cell Signaling) according to manufacturer's instructions. Briefly, tissue samples were dissected and rapidly frozen in liquid nitrogen before further processing. Frozen samples were lysed in cell lysis buffer with brief sonication on ice. Cell lysate was centrifuged at 14,000 rpm for 10 min, and the supernatant was diluted 1:10 in sample diluent and used for incubation with antibody micro-wells according to the manufacturer's protocol. Standard curves were generated using dilutions of a mixture containing equal proportion of all control samples. Relative quantity of total or phosphorylated MAP kinase pathway proteins in Drd1a-cre; miR-128-2fl/fl and control striatum lysates were quantified based on the individual absorbance values at 450 nm. The p-values were calculated using the Welch's test.

Luciferase Reporter Assay

Luciferase reporter assays were performed to measure the repression of RCS and TARPP mRNA expression by miR-128. MicroRNA 3'UTR target reporter plasmids that contain the full length sequences of the RCS and TARPP 3'UTR downstream of a firefly luciferase gene driven by a SV40 promoter for expression in mammalian cells were purchased from GeneCopoeia, MD (pEZX-MT01). Control plasmids containing no 3'UTR inserts were used for comparison. Plasmids contain the *Renilla* luciferase gene to control for transfection and expression efficiency. The sequences of all plasmids were verified by sequencing and restriction enzyme digestion. Reporter or control plasmids were co-transfected with the *Renilla* luciferase plasmids into confluent Neuro2A cells grown in 24-well culture plates with either no miRNA mimic, a miR-124a scrambled control mimic, or miR-128 mimics at the two indicated concentrations (Dharmacon, Thermo Fisher Scientific, USA). Cells were harvested and lysed 24 hour after transfection and cell lysates were assayed for firefly and *Renilla* luciferase activity using Dual-Luciferase Reporter Assay System (Promega, Wisconsin, USA) according to manufacturer's instructions. Firefly luciferase activity was normalized to *Renilla* luciferase activity for each cell culture well and plotted as activity relative to control transfections with no mimics added. At least 3 biological replicates were performed consisting of 3 technical replicates each.

Electrophysiological Analysis

Brain Slice Preparation:

Para-sagittal brain slices (275 μm) were obtained from 3-5 month old male and female Drd1a-TRAP; Drd1a-cre; miR-128fl/fl and Drd1a-TRAP; miR-128fl/fl littermate control mice following procedures approved by the Northwestern University Institutional Animal Care and Use Committee. The mice were anesthetized with a mixture of ketamine (50 mg kg-1) and xylazine (4.5 mg kg-1) and perfused transcardially with 5-10 ml ice-cold artificial cerebrospinal fluid (ACSF) containing (in mM): 124 NaCl, 3 KCl, 1 CaCl2, 1.5 MgCl2, 26 NaHCO3, 1 NaH2PO4, and 16.66 glucose, continuously bubbled with carbogen (95% O2 and 5% CO2). The slices were then transferred to a holding chamber where they were incubated in ACSF containing (in mM) 2 CaCl2, 1 MgCl2, at 35° C. for 60 min, after which they were stored at room temperature until recording.

Electrophysiology:

Patch pipettes were pulled from thick-walled borosilicate glass on a Sutter P-97 puller. Pipette resistance was typically 3-5 MΩ when filled with recording solution. For studies involving bAP propagation, the internal recording solution contained (in mM): 135 KMeSO4, 5 KCl, 10 HEPES, 2 ATP-Mg2+, 0.5 GTP-Na+, 5 phosphocreatine-tris; 5 phosphocreatine-Na+, and 0.1 spermine. The pH was adjusted to 7.25 with NaOH and osmolarity to 270-280 mOsm l-1. For Ca2+ imaging experiments, the recording solution also contained 200 μM Fluo-4 pentapotassium salt and 50 μM Alexa Fluor 568 hydrazide Na+ salt (Invitrogen). For voltage clamp studies, the recording solution contained (in mM): 120 CsMeSO3, 5 NaCl, 10 TEA-Cl (tetraethylammonium-Cl), 10 HEPES, 5 Qx-314, 4 ATP-Mg2, 0.3 GTP-Na, 0.2 Fluo 4 pentapotassium salt and 0.05 Alexa Fluor 568 hydrazide Na+ salt (Invitrogen), pH 7.25, 270-280 mOsm-1. Slices were transferred to a submersion-style recording chamber mounted on an Olympus BX51 upright, fixed-stage microscope and continuously perfused with carbogen-bubbled ACSF. Electrophysiological recordings were obtained with a Multiclamp 700B amplifier. Stimulation and display were obtained as previously described (Day et al., 2008) using the custom-written shareware package WinFluor (John Dempster, Strathclyde University, Glasgow, Scotland, UK), which automates and synchronizes the two-photon imaging and electrophysiological protocols. The amplifier bridge circuit was adjusted to compensate for serial resistance and continuously monitored during recordings.

2-Photon Laser Scanning Microscopy (2PLSM) and Ca2+ Imaging:

2PLSM and Ca2+ imaging were performed as previously described (37). Striatonigral spiny projection neurons (SPNs) were identified by somatic eGFP two-photon excited fluorescence using an Ultima Laser Scanning Microscope system (Prairie Technologies). A DODT contrast detector system was used to provide a bright-field transmission image in registration with the fluorescent images. The green GFP signals (490-560 nm) were acquired using 810 nm excitation (Verdi/Mira laser). SPNs were patched using video microscopy with a Hitachi CCD camera and an Olympus 60×/0.9 NA lens. Alexa 568 fluorescence was used for visualization of cell bodies, dendrites, and spines. Following patch rupture, the internal solution was allowed to equilibrate for 15-20 minutes before imaging. High magnification maximum projection images of dendrites were acquired with 0.072 μm2 pixels with 10 μm pixel dwell time. Approximately 20 images taken with 0.5 μm focal steps. Spine density was calculated from maximum projection images of dendritic segments ~100-120 μm from the soma, as previously described (38). Spines were manually counted and normalized to the length of the corresponding dendrite.

Single bAPs were generated by injecting somatic current pulses (2 nA, 2 ms). Dendritic changes in Ca2+ were measured as ΔF/Fo via line scans, where Fo is the average green fluorescence before the bAP. Peak ΔF/Fo values were obtained from the average of 6 consecutive trials and calculated by a single exponential fit of the Ca2+ transient decay. Green fluorescent line scan signals were acquired at 6 ms per line and 512 pixels per line with 0.08 μm pixels and 10 μs pixel dwell time. The laser-scanned images were acquired with 810 nm light pulsed at 90 MHz (~250 fs pulse duration). Power attenuation was achieved with two Pockels cells electro-optic modulators (models 350-80 and 350-50, Con Optics, Danbury, CT). The two cells were aligned in series to provide an enhanced modulation range for fine control of the excitation dose (0.1% steps over four decades). The line scan was started 200 ms before the stimulation protocol and continued 4 s after the stimulation to obtain the background fluorescence and to record the decay of the optical signal after stimulation. To reduce photo-damage and photo-bleaching, the laser was fully attenuated using the second Pockels cell at all times during the scan except for the period directly flanking the bAP burst. Dendritic line scans were acquired from proximal (~50 µm from soma) and distal (~100-120 µm from soma) dendritic regions for each cell. bAP attenuation was calculated by normalizing distal Ca2+ transient peaks to the maximum proximal Ca2+ transient per cell.

Glutamate uncaging was achieved using a Chameleon-XR laser system (Coherent Laser Group, Santa Clara, CA). 5 mM MNI-glutamate (Tocris, Cookson, Ellisville, MO) was superfused over the slice using a syringe pump and multi-barreled perfusion manifold (Cell MicroControls, Norfolk, VA). Glutamate was uncaged adjacent to individual spine heads using 1 ms pulses of 720 nm light typically 10-20 mW in power at the sample plane. Photolysis power was tuned via a third Pockels cell modulator (Con Optics, Danbury, CT) to achieve uncaged-EPSCs (uEPSCs) averaging 5-10 pA.

Behavioral Analysis

For all behavioral experiments, experimenters were blinded to the genotypes of the animals. All behavior tests have been performed on 4- to 16-week-old mutants and their respective age- and sex-matched littermate controls. All behavior tests were conducted between 7 AM and 7 PM. Genotypes were decoded after data was processed and analyzed. Sample sizes of at least 5 animals were used for behavioral analyses. Subjects corresponding to data points that are more than 2 standard deviations from the sample mean were excluded from analyses. When possible, all littermate animals were included in behavioral experiments as control groups. No randomization protocol was used. Animals were allocated to treatment groups to ensure uniform distribution of ages and sexes in each group. Where 2 conditions are compared, 2-tailed Welch's t-test was used. For comparisons involving multiple sample groups, either 1-way or 2-way ANOVA was used. When a factor had a significant effect, post-tests were performed for pairwise comparisons.

Open-Field Analysis:

Locomotion and exploratory behavior was measured using the open field (40×40×30 cm). Activity was quantified by the computer-operated Photobeam activity system (Accuscan Instruments, Columbia, OH). Mice were recorded for total distance moved in the whole arena and number of vertical episodes (rearing). Open field analysis was performed on 4 week old mice and their respective age and sex-matched littermate controls. To ensure that the experimental mice had no seizures at the time of the analysis, the mice used for the behavioral tests were kept under surveillance for 2 hours prior to the test, during the 1-hour motor test, and 4 hours after the test.

Drugs Used:

Mice were injected intraperitoneally (i.p.) with the microliter volume equivalent of 10× body weight (g). D1-receptor agonist SKF 81297 (Taconic) was diluted from stock (10 mg/ml in DMSO) with 0.9% saline to indicated concentration. MEK inhibitor SL327 (Taconic) was diluted from stock (diluted in DMSO) with 30% DMSO/Saline to indicated concentration. Cocaine (Sigma, C5776) was diluted in water to a 100 mg/ml stock solution. Sodium valproate (Sigma, P4543) was prepared at a 0.26% w/v solution in drinking water for oral administration. Kainic acid (Sigma, K0250) was dissolved in saline just before use to 30 mg/kg concentration for i.p. injections. Picrotoxin (Sigma, P1675) was prepared as a 25 mg/ml stock solution in ethanol and further diluted in saline to inject at a 3 mg/kg concentration for seizure induction.

Home Cage Seizure Monitoring:

Animals were housed in clear plexiglass chambers with pre-installed cameras (Phenotyper, Noldus Information Technology), and provided with food and water ad libitum. Continuous 24-hour video recordings of mice were taken. Video recordings were manually scored for severity, duration and frequency of seizures. To constitute recorded tonic-clonic seizures, mice must cease all normal activity such as walking, sniffing or grooming, adopt a rigid posture with arched back and progress to repeated rearing and falling. A large majority of tonic-clonic seizure episodes progressed to a further stage with rapid running and bouncing behavior, although this was not required for inclusion as tonic-clonic seizure.

Chemically-Induced Seizures:

Mice were injected i.p. with kainic acid (30 mg/kg in saline) or picrotoxin (3 mg/kg in saline) and placed in chambers in isolation and observed for 60 min. after injection. All injected animals rapidly enter period of immobility (Stage 1). Animals were observed for the time of onset of tonic-clonic seizures characterized by repeated rearing and falling followed by running and bouncing, or constant limb movements if postural control is lost.

Survival Curves:

Date of sacrifice or death in the home cage was recorded for mutants and cage mate controls, plotted as Kaplan-Meier survival curves, and compared using log-rank tests.

6-OHDA Lesions:

Mice were anesthetized with ketamine/xylazine. Mice were stereotactically injected with 6-OHDA (3.5 mg/ml in 0.02% ascorbic acid) 2×2 ul in left striatum (ML=−2.1 AP=+1.0 DV=−3.4; ML=−2.3 AP=+0.3 DV=−3.4) and vehicle injection 2×2 ul in right striatum (ML=+2.1 AP=+1.0 DV=−3.4; ML=+2.3 AP=+0.3 DV=−3.4). Mice were single housed for 3 weeks after surgery to allow for recovery before behavioral assays.

Rotational Behavior:

Rotational behavior in lesioned mice was assayed by an experimenter blind to the genotypes for two consecutive 2-min intervals 5 min after i.p. injection of cocaine. Net contralateral rotations are given by total contralateral rotations minus ipsilateral rotations. Data shows average of both readings. After 3 days, the same behavioral assay was recorded in response to SKF81297.

In terms of region specificity, the increase in basal motor activity is regulated by miR-128 in the striatum while depletion in the hippocampus or cortex have only a small or no effect on motor activity (except temporary increase in exploration as seen by first 20 min in EMX-cre mouse line). Seizures and survival are more strongly affected if miR-128 is depleted in the hippocampus and cortex. Applicants therefore over-express miR-128 specifically in cortex or hippocampus and find the strongest seizure suppressing effects without changing basal motor activity.

In one example, the in vivo injectable modified RNA used had the following sequence: mmu-miR-128-3p MIMAT0000140: UCACAGUGAACCGGUCUCUUU (SEQ ID NO: 1) to be modified as indicated: *2'Ome all bases, phosphothioates 2×5' and 4×3', 3'-cholesterol. In vivo HPLC with counter ion (Na+) exchange, sterile filtrations, and endotoxin testing as post synthesis processing 5'mU*mC*mAmCmAmGmUmGmAmAmCmCmGm
GmUmCmUmC*mU*mU*mU*-3'-ChI Efficacy of Ectopic miR-128 Overexpression in Protecting Mice Against Chemically Induced Seizures In Vivo In another example, Applicants test the efficacy of ectopic miR-128 overexpression in the cortex, hippocampus, striatum and thalamus. The time-course and level of miR-128 overexpression is established upon administration of i) miR-128 oligonucleotides, ii) AAV-delivered miR-128, as well as the iii) genetic overexpression of miR-128 in mice in vivo. The local increase in miR-128 expression in the mouse brain is achieved by using a stereotaxic approach. The brain-regions and miR-128 overexpressing approaches are studied to see which has the greatest effect in reducing the sensitivity to chemically-induced seizures in mice in vivo. Applicants use different pro-convulsant agents including picrotoxin, kainic acid, and policarpine to mimic seizures induced by increased excitatory as well as decreased inhibitory tone in neurons. miR-128 overexpression in the hippocampus using the AAV approach displays the highest efficacy.

Treatment of Mouse Models of Severe Human Generalized Childhood Epilepsy Such as the Dravet-Syndrome by Genetic or Ectopic Overexpression of miR-128

The inventors of the instant disclosure ectopically overexpress miR-128 in mouse models of severe human generalized childhood epilepsy such as the Dravet-syndrome (Scn1a or Gabrg2 deficient mice) to establish the efficacy of miR-128 in averting seizures in these mice. Mice with a loss of Scna1 and Gabrg2 display spontaneous seizures and ataxia beginning in the fourth postnatal week followed by premature death from seizure-related cause. Applicants test the effects of miR-128 overexpression on seizure development and survival in three to four week old Dravet-syndrome mice. The ability of genetic miR-128 overexpression in postnatal forebrain neurons to protect mice against spontaneous seizure development is also tested. Secondly, Applicants test the seizure-suppressing ability of oligonucleotide or AAV-based miR-128 overexpression in different brain regions (striatum, temporal cortex, hippocampus, mediodorsal thalamus) to determine whether there are specific locations that can short-circuit brain-wide seizures due to local miR-128 overexpression. Ectopically supplied miR-128 into the neurons of the hippocampus or thalamus protects mice suffering from Dravet-like syndrome against spontaneous recurrent seizures and premature death.

All publications, patents, and patent applications mentioned herein are hereby incorporated by reference in their entirety as if each individual publication or patent was specifically and individually indicated to be incorporated by reference. In case of conflict, the present application, including any definitions herein, will control. While several aspects of the present invention have been described and depicted herein, alternative aspects may be effected by those skilled in the art to accomplish the same objectives. Those skilled in the art will recognize, or be able to ascertain using no more than routine experimentation, many equivalents to the specific embodiments of the invention described herein. Accordingly, it is intended by the appended claims to cover all such alternative aspects as fall within the true spirit and scope of the invention.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

REFERENCES

1. M. He et al., Neuron 73, 35 (Jan. 12, 2012). 2. N. Y. Shao et al., BMC genomics 11, 409 (2010). 3. E. A. Miska et al., Genome biology 5, R68 (2004). 4. A. M. Krichevsky et al., RNA 9, 1274 (October, 2003). 5. C. R. Gerfen. Annual review of neuroscience 15, 285 (1992). 6. A. V. Kravitz et al., Nature 466, 622 (Jul. 29, 2010). 7. M. R. Fabian et al. Annual review of biochemistry 79, 351 (2010). 8. A. Schaefer et al., The Journal of experimental medicine 207, 1843 (Aug. 30, 2010). 9. S. W. Chi. Nature 460, 479 (Jul. 23, 2009). 10. D. P. Bartel, Cell 136, 215 (Jan. 23, 2009). 11. M. Heiman et al., Cell 135, 738 (Nov. 14, 2008). 12. S. van Dongen et al., Nature methods 5, 1023 (December, 2008). 13. A. Grimson et al., Molecular cell 27, 91 (Jul. 6, 2007). 14. J. G. Doench, Genes & development 18, 504 (Mar. 1, 2004). 15. M. J. Brodie, Seizure: the journal of the British Epilepsy Association 19, 650 (December, 2010). 16. J. W. Ramos et al., Molecular biology of the cell 11, 2863 (September, 2000). 17. A. Matsuda et al., Oncogene 22, 3307 (May 22, 2003). 18. S. V. Rakhilin et al., Science 306, 698 (Oct. 22, 2004). 19. S. P. Megraw M et al., Theor Chem Acc, 593 (2010). 20. J. D. Sweatt, Current opinion in neurobiology 14, 311 (June, 2004).

21. G. M. Thomas, et al. Nature reviews. Neuroscience 5, 173 (March, 2004). 22. E. Valjent, et al., BMC neuroscience 7, 20 (2006). 23. A. S. Nateri et al., The EMBO journal 26, 4891 (Nov. 28, 2007). 24. C. Mazzucchelli et al., Neuron 34, 807 (May 30, 2002). 25. C. R. Gerfen et al., The Journal of neuroscience: the official journal of the Society for Neuroscience 22, 5042 (Jun. 15, 2002). 26. M. Feyder et al., Frontiers in behavioral neuroscience 5, 71 (2011). 27. M. A. Cenci et al., Progress in brain research 183, 209 (2010). 28. D. S. Kim et al., The Journal of neuroscience: the official journal of the Society for Neuroscience 20, 4405 (Jun. 15, 2000). 29. M. A. Blair et al., Epilepsia 52, 993 (May, 2011). 30. B. A. Chioza et al., Epilepsy research 87, 247 (December, 2009). 31. Y. Sasaki et al., Immunity 24, 729 (June, 2006). 32. E. Casanova et al., Genesis 31, 37 (September, 2001). 33. S. Gong et al., Nature 425, 917 (Oct. 30, 2003). 34. H. Li, Bioinformatics 25, 1754 (Jul. 15, 2009). 35. X. Ji et al., Nucleic Acids Res 34, W551 (Jul. 1, 2006). 36. P. Machanick et al., Bioinformatics 27, 1696 (Jun. 15, 2011). 37. B. Langmead et al., Genome Biol 10, R25 (2009). 38. M. Day et al., The Journal of neuroscience: the official journal of the Society for Neuroscience 28, 11603 (Nov. 5, 2008). 39. C. S. Chan et al., The Journal of neuroscience: the official journal of the Society for Neuroscience 32, 9124 (Jul. 4, 2012).

What is claimed is:

1. A method for treating or reducing the likelihood of the development of temporal lobe epilepsy in an individual at risk for developing epilepsy, comprising administering to said individual an agent, wherein
said individual has suffered a traumatic brain injury or a brain injury caused by a stroke,
the agent comprises a seed region of microRNA (miR)-128 or a polynucleotide encoding a transcript wherein the transcript comprises the seed region of miR-128, and
the seed region of miR-128 consists of nucleotides 2 through 7 of SEQ ID NO: 1.

2. The method of claim 1, wherein the agent is administered intrathecally or intranasally.

3. The method of claim 1, wherein the agent is administered to the central nervous system of the individual.

4. The method of claim 1, wherein the agent comprises the seed region of miR-128.

5. The method of claim 4, wherein the agent further comprises a polynucleotide with 90 percent or more sequence identity to SEQ ID NO: 1.

6. The method of claim 4, wherein the agent further comprises a chemically stabilized polynucleotide.

7. The method of claim 1, wherein the agent comprises the polynucleotide encoding the transcript.

8. The method of claim 7, wherein the transcript further comprises a polynucleotide with 90 percent or more sequence identity to SEQ ID NO: 1.

9. The method of claim 7, wherein the agent further comprises a viral vector.

10. A method for treating or reducing the likelihood of the development of epilepsy in an individual at risk for developing epilepsy, comprising administering to said individual an agent, wherein said individual has suffered a traumatic brain injury or a brain injury caused by a stroke,
the agent comprises a seed region of microRNA (miR)-128 or a polynucleotide encoding a transcript wherein the transcript comprises the seed region of miR-128, and
the seed region of miR-128 consists of nucleotides 2 through 7 of SEQ ID NO: 1.

11. The method of claim 10, wherein the agent is administered intrathecally or intranasally.

12. The method of claim 10, wherein the agent is administered to the central nervous system of the individual.

13. The method of claim 10, wherein the agent comprises the seed region of miR-128.

14. The method of claim 13, wherein the agent further comprises a polynucleotide with 90 percent or more sequence identity to SEQ ID NO: 1.

15. The method of claim 13, wherein the agent further comprises a chemically stabilized polynucleotide.

16. The method of claim 10, wherein the agent comprises the polynucleotide encoding the transcript.

17. The method of claim 16, wherein the transcript further comprises a polynucleotide with 90 percent or more sequence identity to SEQ ID NO: 1.

18. The method of claim 16, wherein the agent further comprises a viral vector.

19. The method of claim 10, wherein said individual has suffered a traumatic brain injury.

20. The method of claim 10, wherein said individual has suffered a brain injury caused by a stroke.

* * * * *